(12) United States Patent
Ofek

(10) Patent No.: US 8,805,489 B1
(45) Date of Patent: Aug. 12, 2014

(54) PERSONAL MEANING EXTRACTION

(76) Inventor: Einat Ofek, Yokneam (IL)

( * ) Notice: Subject to any disclaimer, the term of this patent is extended or adjusted under 35 U.S.C. 154(b) by 451 days.

(21) Appl. No.: 13/023,108

(22) Filed: Feb. 8, 2011

Related U.S. Application Data

(60) Provisional application No. 61/302,185, filed on Feb. 8, 2010.

(51) Int. Cl.
*A61B 5/04* (2006.01)

(52) U.S. Cl.
USPC .......................................... 600/544

(58) Field of Classification Search
USPC ............................... 600/545, 544
See application file for complete search history.

(56) References Cited

U.S. PATENT DOCUMENTS

| | | | |
|---|---|---|---|
| 2008/0097235 A1 | 4/2008 | Ofek | |
| 2009/0326405 A1* | 12/2009 | Makinen | 600/544 |
| 2010/0069775 A1* | 3/2010 | Milgramm et al. | 600/544 |

OTHER PUBLICATIONS

Ofek E, Pratt H. A questionnaire for quantifying subjective significance of names: physiological validation with PAT. Physiol Behav. 2008;94(3):368-73.
Ofek E, Pratt H. Neurophysiological correlates of subjective significance. Clin Neurophysiol. 2005;116(10):2354-62.
Wunderlich JL, Cone-Wesson BK. Maturation of CAEP in infants and children: A review. Hearing Research 2006;212(1-2):212-23.

* cited by examiner

*Primary Examiner* — Navin Natnithithadha
*Assistant Examiner* — Etsub Berhanu

(57) ABSTRACT

The present invention comprises a method and system for identifying personal meaning of an auditory stimulus to the person, such as, but not limited to, passion, using the measurement and processing of EEG and the identification of the presence of specific patterns in the signal.

19 Claims, 24 Drawing Sheets

FIG. 1

PERSONAL MEANING EXTRACTION

FIELD OF THE INVENTION

Embodiments of the present invention relate to a method and a system to extract the personal meaning of an auditory stimulus to a person through obtaining patterns by measurement of EEG.

BACKGROUND

Event related potentials (ERP) were chosen as the main tool for this non-invasive approach to motivational (emotional) processes in the human brain. Other methods, such as NIRS or fMRI may be included at a later stage. ERP are scalp potentials, derived from the EEG (Electro-Encephalo-Graph) by averaging time-locked activity in response to a stimulus. The significant advantage of the EEG for functional imaging is its time resolution, in the order of milliseconds. This is the time scale in which cognitive (and emotional) processes take place. Human EEG was first recorded by Hans Berger, in 1925. Evoked potentials have been used in neuroscience and in clinics for over 40 years. Its high temporal resolution (in the order of milliseconds) in addition to its availability in measuring brain activity in healthy people (the method is non invasive), make it very suitable to measure neural activity associated with cognitive and emotional processes in humans.

SUMMARY OF THE INVENTION

One embodiment of the present invention comprises methods and systems for identifying the personal meaning of an auditory stimulus to a person, including identifying true passion (i.e., ultimate passion), using EEG measurement while the user is exposed to auditory test stimuli, including at least one auditory test stimulus. Stimuli are presented through the auditory modality, such as by earphones, or by some other method. Thus, identified patterns in the EEG which are evoked by certain stimuli are linked to a database of patterns and their associated personal meanings and the personal meaning of a certain stimulus to a certain person is inferred. This can be done for any person to infer personal meanings of any auditory stimulus. This is done by recording EEG at the time are after presentation at least one auditory stimulus, identifying the presence of specific patterns in the signal, and relating these patterns to a given list, or database, of patterns and their associated personal meanings. This can be done also when the person has difficulties in communication. This can be done also to answer a question to which the person has no clear conscious answer, or when the person is uncertain of the answer to the question.

Some of the embodiments comprise the following:
1. Initial database of patterns associated with certain personal meanings.
2. A method for extracting existing patterns for a certain person for a certain auditory stimulus.
3. A method for growing the database by identifying new patterns associated with new personal meanings.

The method of extracting patterns for a certain person related to specific stimuli comprises the steps of choosing and preparing auditory stimuli, then attaching sensors and measuring EEG at the same time or after the person is exposed to the auditory stimuli. The process comprises: choosing a stimulus, or stimuli, recording signal and then obtaining patterns. The signal can be analyzed to obtain patterns. The received patterns can be compared to a database of patterns. An answer may be given to the user or to a third party, whether the recorded patterns resemble one or more of the patterns in the database, and an explanation may be given as to the meaning of the received patterns, such as that this specific stimulus is related to the true, or ultimate, passion of the user or not; or—that this is what the user wants, consciously or unconsciously, or some other answer, depending on the stimuli and on the obtained patterns. Multiple answer questions can be answered such as—"What is the thing I like the to do in life . . ." out of a number of selected test stimuli. These answers may be used for therapy, for entertainment, for diagnosis, for communication, for research, for self development, or for some other use. To summarize, the user or a third party propose a question, relevant auditory test stimuli are chosen and EEG is measured and recorded while or after the user is exposed to at least one auditory test stimulus. The EEG may be analyzed to obtain specific patterns. The patterns may be compared to a given database of patterns, such as the one described in this patent application, to determine the personal meaning of the test stimulus or stimuli to the user person. Such a meaning may be the identification of the presence of true, or ultimate, passion, regarding specific stimulus. Other questions may be answered, such as "what do I want"; "what is my best choice". The responses and answers to those questions are obtained from the brain (conscious and unconscious) of the user, by the measurement of at least one biological signal. The questions may be asked by the user, or by a third party, regarding the user. True, or ultimate, passion—for which the term "passion" may be used herein—signifies here what the person truly wants, with or without obstacles, whether he is conscious or unconscious of that wish. In other words, it is what the person truly wants in his "heart", beyond any fear or hesitation or conscious thought that might hide that from the person. This is the thing that the person truly wants to experience or to have—not just like to have or to experience, but strongly wants that. The database may grow to include more specific patterns related to specific personal meanings. One way to grow the database is also described here.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments of the present invention only, and are presented in the cause of providing what is believed to be the most useful and readily understood description of the principles and conceptual aspects of embodiments of the invention. In this regard, no attempt is made to show structural details in more detail than is necessary for a fundamental understanding of the embodiments; the description taken with the drawings making apparent to those skilled in the art how the several forms of the invention may be embodied in practice. In the accompanying drawings:

Figure 1:
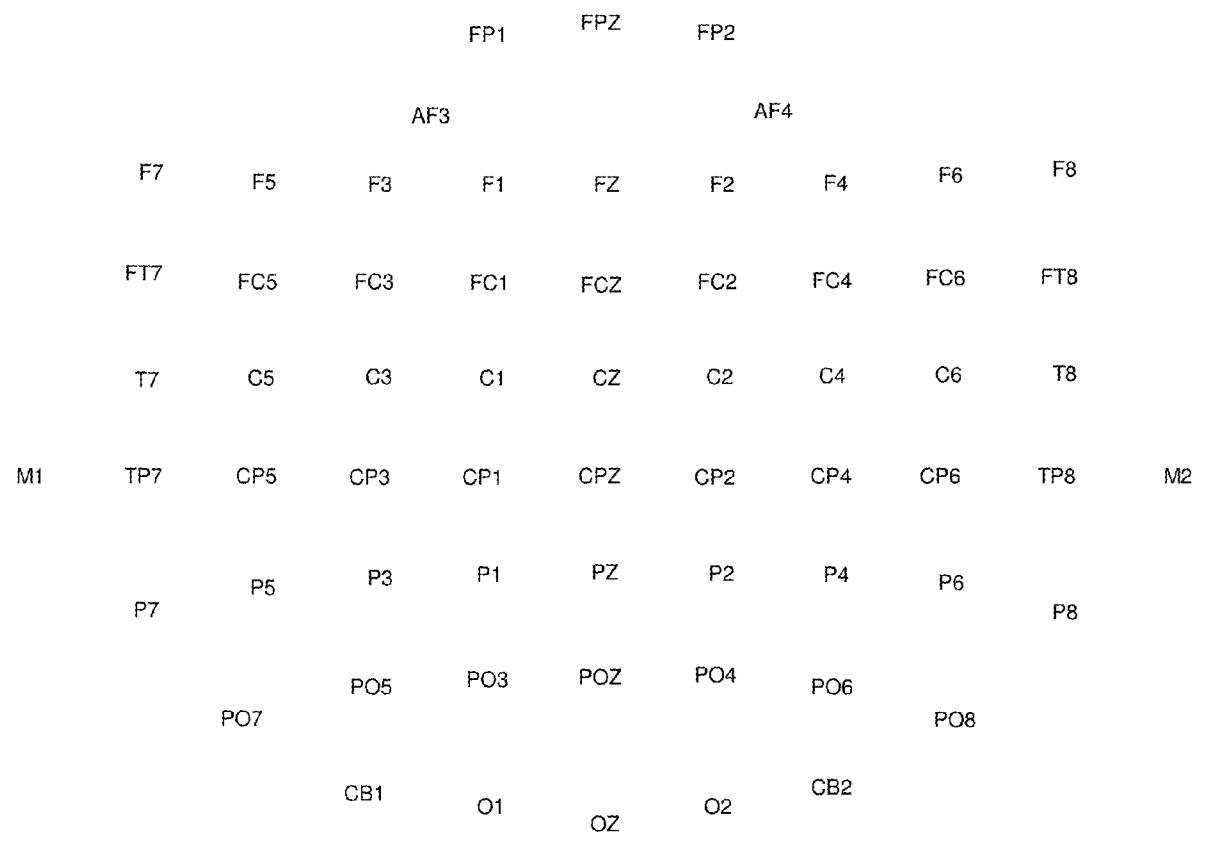

FIG. 1 schematically shows the positioning of all electrodes, according to the 10/20 positioning adapted for 64 electrodes.

DETAILED DESCRIPTION OF THE INVENTION

Figure 2:
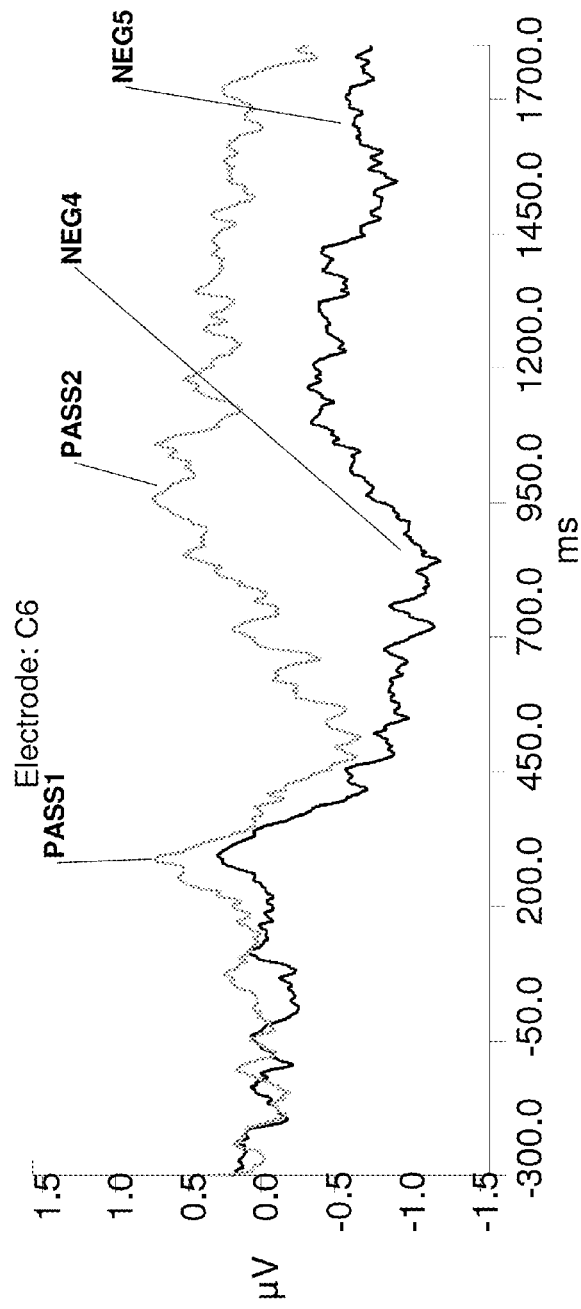
FIG. 2 schematically shows voltage detected in Electrode C6 vs. time.
Figure 3:
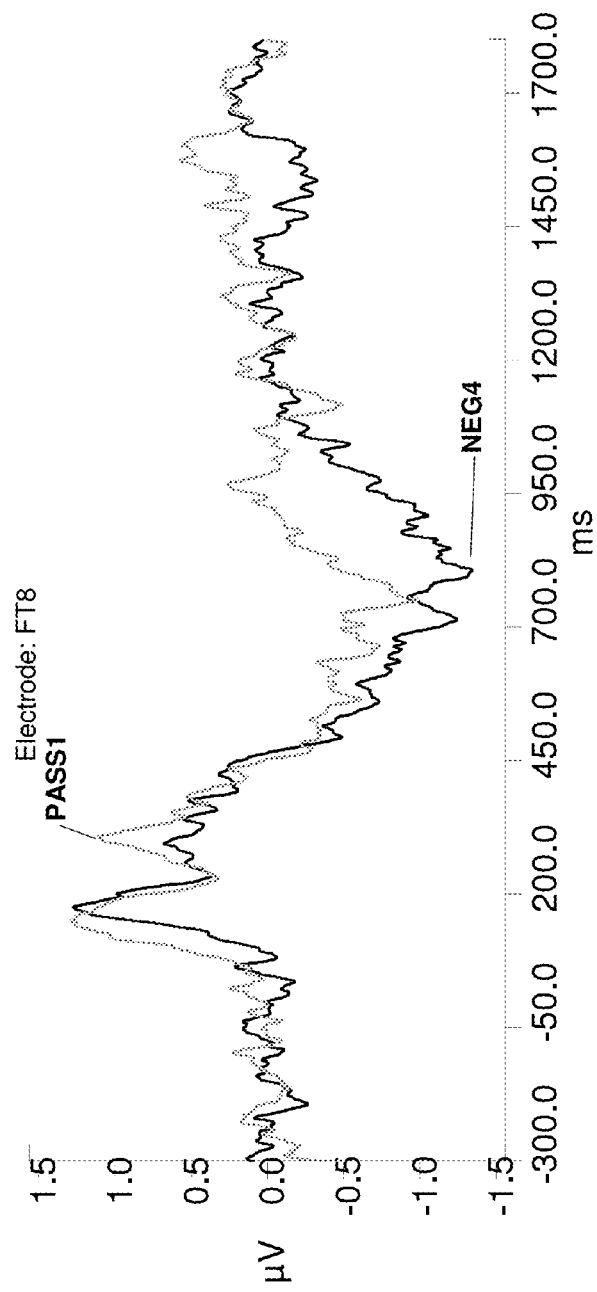
FIG. 3 schematically shows voltage detected in Electrode FT8 vs. time.

1.

EEG, a measure of brain activity, is measured in a response to a list of auditory stimuli or words comprising of at least one auditory stimulus, or word. The embodiment comprises of how to measure brain activity, how to identify brain activity patterns (BAP), and how to generate a list of test words.

After measuring brain activity, the presence of specific brain activity patterns is noted for each word. Those brain activity patterns are linked to a database of brain activity patterns and their associated personal meanings, such as the one suggested here. For each personal meaning there are specific associated brain activity patterns (BAP)—which can be included in a database of BAP associated with personal meanings. So, for personal meaning X (such as ultimate true passion), brain activity patterns X1, X2, X3 are associated. A certain stimulus carries a certain personal meaning for the person if at least one BAP associated with this personal meaning is present in the response to the stimulus.

2.

Some of the disclosed embodiments are directed towards identifying passion that the person has, concealed or unconcealed, conscious or unconscious. This may be used in situations of obscured communication, such as in autism spectrum disorders (ASD), Alzheimer, or for people with psychiatric disorders, to find what the person really wants or cares about. It can also be used to help life coaches or therapists or doctors or other professionals treat their clients better, through understanding their clients better, communicating with them better and providing them a better service and therapy. It can also be used by a private individual, as an entertainment or for self development, finding true goals and then achieving them. It can also be used to control computer games or applications. The personal meaning of a stimulus, or an object, or a word to a person may be inferred using this method for any use.

BAP are extracted in response to stimuli, and then linked to a database of BAP and their associated personal meanings. Thus, each stimulus is connected to a personal meaning, based on its extracted BAP.

The output of this can be used by the user to answer his or her own or a third party's questions.

3. Questions

A question, to which there is a partial or a complete answer in the brain, unconscious, subconscious or conscious, of the tested person, can be answered. Thus, a question which is meaningful to the tested person may be answered.

The following questions may also be answered by this method:

What is the thing that is more important to me?
What do I like?
Where do I want to get?
What prevents me from getting there?
What do I like more out of a list of items?
Does that thing have a negative connotation for me?
Does that thing have a positive connotation for me?
What is my best choice?
What should I do now?
What is the best way for me to succeed?

4. An Example of Use

For a person that cannot communicate—for the question "What do you want?"; Test stimuli will be chosen based on general knowledge, or some statistical knowledge about that person, such as age, gender, family, culture or some other knowledge. BAP will be extracted in response to the test stimuli, and will be compared to a database of BAP and their associated personal meanings.

An example of a way to use an embodiment of the invention, for a tested person, or user, that can communicate to some degree, is the following.

A method to answer the question "What do I want"?
  1. The software or the therapist or a friend or the tested person himself or herself can ask the tested person further questions:
      1. "In which field?"
      2. The answer to that may be "In my life now".
  2. The software or the therapist or a friend or the user can ask the user further questions:
      1. "What are the things and the people that are present in your life now?"

2. "What are the things you may want to have? Please give a large list of possible things, including things you don't know or you hesitate about".
3. An example of a possible answer may be—(1) present—"Work, Partner, Boss, House"; (2) Things that I may want—"Children, Success, Papers, Book, Family, Career, Vacation".

3. Relevant stimuli will be chosen based on the things and the people suggested. For this specific example, these stimuli may be the following words:
    1. Things that the user has in life: "Work, Partner, Boss, House"
    2. Things that the user may want: "Children, Success, Papers, Book, Family,
    Career, Vacation".
4. All those words will be included in the test as potential stimuli. In addition to these, it is optional to include more stimuli, chosen by the user or by a third party, as (1) potential non meaningful stimuli or (2) matched stimuli—matching the previously chosen stimuli semantically, syntactically and phonetically. As such, for the word Success, the words "strength" and "support" may be chosen as matched words.

For one person, the word "Success" may have the personal meaning of "something that I want very much and I aspire to"; for another person the words "support" or "strength" may have this same personal meaning or some other personal meaning.

5. Other ways to choose stimuli for a person are the following:
    1. The software will choose the stimuli on a statistical basis for the user, based on his personal details, such as age, culture, occupation, family information or some other details.
    2. A third party will be interviewed about the user.
    3. The user or a third party will choose stimuli from a given database of stimuli.
6. The chosen stimuli will be prepared for administration (or they may be ready beforehand), through the auditory modality.
7. The stimuli are presented through the auditory pathway. The stimuli may be prepared and recorded beforehand or recorded by user, third party, or software. It is better that all stimuli are recorded by the same reader.
8. EEG is recorded by sensors at the time of presenting the chosen auditory stimuli. The time of each stimulus presentation is recorded as well.
9. EEG (as a measure of brain activity) can be analyzed.
10. The presence of patterns in the recorded signals is identified for each stimulus separately and or for groups of stimuli, as described below.
11. The identified patterns are compared to a database of BAP and their related personal meanings, such as the one proposed here.
12. Personal meanings are ascribed to the stimuli.
13. From the list of stimuli used, stimuli having more BAP linked with a personal meaning such as passion associated with them, or having BAP with greater amplitudes, or BAP involving more electrodes, are stimuli that the tested person may want more. For example, if the word "house" has more BAP associated with passion in response to it, with greater amplitude and involving more electrodes, than "house" is likely to be something that the tested person likes, or likes to have.

5. A Method to Extract BAP

The following is a description of one way to extract patterns in response to a stimulus. The BAP can be extracted through measuring event related potentials (ERP)—then the patterns may be spatiotemporal voltage patterns. Such patterns may be the latencies, amplitudes and locations of peaks (maxima or minima) in the ERP. BAP can be extracted by some other EEG analysis technique.

Patterns can be extracted after processing of ERP from the recorded EEG, as described herein. Patterns can be present in specific groups of electrodes as the ones suggested here.

A BAP can be a voltage peak in a certain time window in a certain electrodes group. The presence of specific peaks in those electrodes in specific time frames may mark the presence of specific patterns associated with specific personal meanings. The specific presence of peaks in response to test stimuli can also be detected through comparison of the response to the test stimulus or stimuli in one or more electrodes to the following: (1) the averaged response of this person across all stimuli used, marking the presence of peaks that are specifically in response to the one test stimulus and not to all stimuli averaged together. (2) Response to other stimulus or stimuli. (3) Recordings from other electrodes. (4) A given list of known neutral stimuli. (5) A baseline period recorded at that electrode before the stimulus. (6) A measured SD (standard deviation) in this electrode across all the recorded time for this stimulus, or for all stimuli. A pattern can be identified when a peak is present and this peak amplitude is greater than a*SD, for a specific chosen 'a'>0. "A" can equal 2 in this example.

A peak that was identified in a single electrode, which is part of a given list of patterns associated with a certain meaning, is marking the presence of one identified pattern associated with that meaning. The personal meaning thus identified can be stronger if more of the following features exist for it:
   Presence of more patterns associated with this personal meaning in the database.
   Presence of this pattern in more electrodes out of the designated electrode group.
   Greater amplitude of the pattern that is recognized.

Different groups of patterns are related to different personal meanings: An example of possible personal meanings is the following: "negative connotation, positive connotation, Somebody I love, Something I like, Past traumatic event, Values that are important to me, relation to ultimate true passion, or generally emotional".

6. A Method to Add BAP to the Database

The following is a description of one way to add additional patterns to the database.
    1. Interview the person or a third party to collect potential stimuli, then measure EEG (related to brain activity) before, during and after administration of auditory stimuli. After the measurement of the signals, or beforehand, the tested person or a third party can be interviewed, or personal information may be collected in another way, as from documents. The personal meaning of each stimulus will be determined based on this information that was collected and/or the interviews. BAP will be identified in response to each stimulus. The BAP will be related to the known personal meanings of each stimulus, and a database will be built of the personal meanings and the BAP that were found in response to them. This can be done in a large group of tested people to validate the database.
    2. If the signal is EEG, processed to obtain ERP, then the process of adding patterns to the database may include the following: ERP will be extracted from the EEG in response to the auditory test stimuli, and BAP identified to each stimulus for each person. A database will be built connecting the personal meanings across people, gained through interviews or by other method, to BAP found in all people, in response to stimuli conveying the same personal meanings across people. The database that is built will be used to classify the BAP of new examined people (individuals) after-wards.

3. Such new personal meaning may be "something that interests me"; "something that I desired in the past"; "something that I used to be interested in the past"; "something that can bring benefit to my life"; "something that is required in my life"; "Something that is related to things I loved in the past"; "something that is related to past trauma" and other personal meanings. The personal meaning of those stimuli can be isolated through questionnaires and interviews of the person and a third party.

4. The method to identify new BAP to be connected to new personal meanings is the following. For each new personal meaning X, the ERP of all examined people to different stimuli conveying personal meaning X to each of them (different stimuli will convey personal meaning X for different people), will be measured. BAP that are present for more than one person, in the response to stimuli conveying personal meaning X, and not to other stimuli, having similar physical properties but not the personal meaning X, will be included in the database, for personal meaning X. BAP present in ERP may be the presence of a peak in the ERP in certain electrode or electrodes group at a certain time window after stimulus onset. This BAP will be chosen as relevant to personal meaning X if it is present for stimulus, or stimuli, conveying personal meaning X for a person or a group of people, and not present for other stimuli, having similar physical properties, but not conveying personal meaning X for that person or group of people. The link of the BAP to personal meaning X is stronger if this BAP is present in a large group of people, for different stimuli conveying personal meaning X for each of them. Some BAP related to a certain personal meaning may be present in some people but not in all people. Therefore, a combination of BAP connected to personal meaning X may be present in a certain person, including some but not all of the BAP linked to personal meaning X, and still that stimulus to which some of those BAP are present will be linked to personal meaning X.

7. A Suggested Method to Process ERP

The following is a description of a suggested way to analyze ERP:

Record EEG from at least one recording electrode of any type at the time of presenting at least one specific auditory stimulus at least once. Additional electrodes can be used, such as a Ground electrode, that may be connected to the forearm, a Reference electrode, that may be connected to the nose or to another location. Possibly EOG (Electrooculogram) electrodes may be connected below and/or above the eye. For ERP measurement, it is suggested to present at least 20, or even 70 repetitions of the stimulus or a group of stimuli in order to average them together later. The EEG can be cut before and after the stimulus. Baseline may be adjusted using a period of EEG recording before the stimulus. Ocular artifacts may be corrected using the EOG electrode if used. The EEG may be filtered. For example LPF may be used at 24 Hz. The electrodes measured may be referenced to one reference electrode, or to an averaged reference of some or all electrodes. If more than one repetition was used then the EEG can be averaged in response to a certain stimulus, or to a group of stimuli.

Thus, the processing, or analysis of EEG to ERP may include one or more of the following steps:
1. Record EEG and mark stimuli administration times.
2. Cut EEG before and after each stimulus.
3. Merge different segments of the EEG to create one file, or several files.
4. Filter EEG segments (for example, LPF 20-24 Hz)
5. Adjust EEG segments in relation to a baseline before the stimulus (for example, the segment between 300 ms to 200 ms before the stimulus can be taken as a baseline).
6. Extract similar EEG segments (in response to the same stimulus or a group of stimuli).
7. Average EEG segments in response to the same stimulus or to a group of selected stimuli.
8. Convert EEG files to ASCII for further analysis.

The ERP voltage over time in each electrode or in groups of electrodes is measured.

After this process of ERP analysis which includes all of the aforementioned steps or some of them, the presence of specific patterns in the ERP waveform is identified, as described above. Then according to the patterns that were found, using the database included here or developed according to the steps mentioned here above, personal meanings are linked to the presented stimuli.

8. Questionnaires for Determining Personal Meanings to Supplement the Database

The following questionnaires may be used to determine a personal meaning of a stimulus to the person, to be related later to BAP. These questions may be used by a third party or by the tested person:
  a. Do you have a good memory that you can tell me about?
  b. Can you tell me about the happiest time of your life?
  c. Do you have any memory which disturbs you? Can you tell me a little about it?
  d. Can you tell me about the worst time of your life?
  e. Who are the people who are closest to you?
  f. Are there people you don't like? Who are they?
  g. Can you tell me about people who hurt you?
  h. Can you tell me about people that you hate?
  i. What are the things which you want? Now and for the rest of your life? What are the things you wish for?
  j. Can you tell me about things which are important to you?
  k. Please go over a list of words, and select 3 words or more that are important to you (such a list may include words such as "success"; "family"; "money" and other words.

These questions can target the following features of stimuli—(1) positive; (2) negative; (3) related to a personal passion. Questions 'a', 'b', 'e' are related to positive stimuli. Questions 'c', 'd', 'f', 'g', 'h', are related to negative stimuli. Questions 'i', 'j' and 'k' are related to "passion" stimuli. Positive words may relate to a happy memory, or to people that the person likes. Negative words may be related to a bad or traumatic memory, or to people the person doesn't like, or that have hurt him or her. Passion words may be related related to important things the person wishes for, or things that are important to the person.

In addition to these questions, other questionnaire may be used to assess the personal meaning of words, or names for example—Ofek E, Pratt H. A questionnaire for quantifying subjective significance of names: physiological validation with PAT. Physiol Behav. 2008; 94(3):368-73. The utilization of this questionnaire is explained for example in—Ofek E, Pratt H. Neurophysiological correlates of subjective significance. Clin Neurophysiol. 2005; 116(10):2354-62.

9. A Method for Developing Database:

A questionnaire or interview using 1 or more questions may be used, in order to extract relevant stimuli to be used in the examination. An example of such a potential questionnaire is included here. The questionnaire included here can be used to identify words that are potentially (1) positive to the individual person; or (2) negative to the individual person; or (3) related to a passion the individual person has.

After the questionnaire—containing one or more questions is delivered, a quick and simple analysis of the answers would yield potential words, names and other stimuli to be used in the examination. If the person does the examination to himself or herself, he knows potentially the relevant stimuli to be utilized, and there is no need in any questionnaire. Also, a given database of stimuli, or words may be used for selecting relevant stimuli, and then also there is no need in such a questionnaire. If a questionnaire is used, potential words to be used as test stimuli may be words that the individual person used in his answers to the questions. Such as "Who are the closest persons to you?" "Sarah is". Then the name "Sarah" can be used as an auditory stimulus.

Potentially, control stimuli, or words, may be selected and added to the stimuli list at this stage. Those control stimuli are ideally selected from a stimuli database. The control stimuli would ideally have similar physical properties to the auditory test stimuli. The response to the test stimuli may be processed and analyzed also without any control stimuli, based only on the presence of one or more of the patterns such as those described here.

Preparation of stimuli. In this stage, the stimuli are prepared for presentation in the auditory modality. For auditory presentation the stimuli may be recorded, or chosen from a given database of recorded auditory stimuli. If the stimuli are recorded, they may be further processed—such as to cut at the beginning of the stimulus, to set the stimulus volume, to noise filter, or some other steps. It is preferred that the stimuli would physically resemble each other, so that the main difference between them is the semantic difference or the difference in personal or emotional content, but that is not obligatory. At least one auditory stimulus will be presented.

There will be at least one repetition of each stimulus. There is no limit to the number of repetitions. The data is more noise-free with a larger number of repetitions used for averaging the signal. Different methods may be used to reduce noise, and then a lesser number of repetitions may be required. A minimal number of repetitions of 20 is suggested, but not obligatory. Between each stimulus to the next there can be no break at all (each stimulus comes immediately at the end of the previous) or there can be a break between them of any time from a few milliseconds to a few seconds or more.

For ERP, it is common to have at least 20 repetitions, and to have about 500 milliseconds between each stimulus to the next.

The prepared auditory stimuli are entered to a presenting device—such as a computer, connected to some auditory output device such as earphones, loud speakers, or some other method. The presenting device is ideally connected to a recording computer, by which the EEG will be recorded. The same device may be used for recording and for presenting. If the stimuli are selected from a database of auditory stimuli, they can be directly entered into the presenting device.

EEG sensors are used to measure and record the EEG and are connected to the examined person. The EEG is recorded, ideally at the same time or after that the stimuli are presented, with at least one repetition upon each stimulus.

ERP are processed, as described herein at the same time that the recording is taking place or after.

The electrophysiological patterns described herein, are identified, at the same time that the recording is taking place or after.

Potential analysis steps for electrophysiological signal—EEG—may include the following steps:
Cut the signal locked in time to the stimuli presentation time.
Use a period just before the stimulus as a baseline
Filter the signal, such as LPF 24 Hz or other.
Use a reference electrode or central averaged reference or any other.

Presence of one or more of patterns from a database such as the one included here in the analyzed signal is detected.
Other patterns may be present such as by using signals other than electrophysiological signals.
If control stimuli are used, the response to control stimuli may be compared to the response to test stimuli, in order to identify the presence of patterns.
If a certain pattern from the database is present for a certain stimulus, then this stimulus is likely to have the personal meaning which is associated with this pattern.

Stimuli for which the patterns are detected, are marked as stimuli related the certain personal meaning, consciously or subconsciously.

An output can be delivered by some means.

The whole process may be repeated to gain more and more specific information.

10. Utilizations

Embodiment of this invention can be utilized in the following ways—

For the diagnosis, assessment and treatment of a psychiatric or psychological condition For the diagnosis, assessment or treatment of a neurological or psychiatric conditions For drug management, especially in neurology and psychiatry, or neuropsychology.

For assessment of people with brain injury or damage, including brain tumor or stroke.

For Assessment and diagnosis of people in coma, or locked in syndrome.

For diagnosis, assessment and therapy to child behavioral or cognitive disorder or disability, including ASD and ADHD (Attention Deficit Hyperactivity Disorder).

For neurological condition

For somebody facing a life changing event

For people with communication disability, such as ASD, coma, locked in syndrome, Alzheimer. Since there is no need for behavioral response in our paradigm, though it may be included in some cases, then people who cannot otherwise well communicate can use this invention too.

For people looking for a new or first job

For people interested in self development.

To restore ex-prisoners to normal life.

To restore patients coming out of mental institutions, or after a psychological crisis, to come back to life and to the society.

For people who would like to earn more money or to be more efficient.

To increase happiness and satisfaction.

For people who want to understand themselves better.

For truth detection

For veterinary applications

As a marketing projection tool

For home consumers, such as for self development, brain computer interface, computer gaming, or other entertainment, application or development.

For biometric assessment.

Security

Communication between 2 or more different people, through some application such as computers or smart phones and network, using brain activity to communicate.

Smart homes

Additional description of potential utilization of the disclosed embodiments includes, but is not limited to:

1. Psychotherapy—
    Assessing traumatic experiences, and also what is important to a patient. This can shorten analysis (psychotherapy) times and make it more efficient, by finding what is significant and important to a patient, even if unconsciously, and by identifying a traumatic experience and its details.
2. Psychiatry—diagnosis and drug management—
    Some embodiments of this invention can provide psychiatry with a scientific method to advance the therapy and diagnosis. Some embodiments of this invention may allow a more accurate diagnosis, and also better drug choice and dosage. In addition, some embodiments of this invention can allow better communication with the patients, by finding what is meaningful to them and what is related to a traumatic experience that might have preceded the disorder.
3. Improve communication with comatose patients—
    Aiding in communication with locked in and comatose patients, by finding what is personal positive and what is personal negative to them, and then allowing better treatment which might aid in their healing process.
4. Improve communication with people with ASD—
    Bridging communication difficulties. The tool can identify objects or stimuli that are personal-emotional to the person. Thus, some embodiments of this invention can overcome and bridge communication difficulties, by identifying the person's emotional response to certain things. Some embodiments of this invention can also identify what the participant wants, or what is related to a traumatic experience he or she had in the past, and thus help in taking care of and treating the person with ASD. The same method can be applied for any other person with communication difficulties, not just ASD.
5. Improving communication with people with Alzheimer—
    Providing better care of Alzheimer patients, and save money while providing them care. Some embodiments of this invention can identify the source of pain or discomfort (agitation) in the less communicating person with Alzheimer, or in any other person for whom identification of source of discomfort or pain is needed. This may aid in choosing the right treatment for this person. Many times, people with Alzheimer are agitated, which costs a lot of money to handle. The source of agitation cannot easily be found for these less communicating patients. Some embodiments of this invention can bypass the communication difficulty and identify the source of agitation, by presenting auditory stimuli, measuring EEG, identifying patterns and comparing to a database of personal meanings of patterns, such as the one suggested here, especially for negative personal emotional meaning. In addition, some embodiments of this invention allow to identify a remnant brain response to family members, even when the patient can no longer behaviorally identify his or her loved ones. This is done by presenting the person with Alzheimer with stimuli related to his or her loved ones, such as first names, or some other auditory stimuli, measuring EEG, identifying the presence of patterns, and comparing the patterns to a database of the personal meanings of patterns, such as the one suggested here. For example, if a combination of the POS# patterns is present for the first name of the spouse, than it is likely that there is remnant brain activity in the brain of the person with Alzheimer, related to his or her spouse, even if there is no longer a behavioral (recognition) response to the spouse. As mentioned herein for people with ASD, it is possible to identify stimuli which are positive personal-emotional or negative personal-emotional to the person, and thus provide a better care for him or her.
6. Lie detection—
    An embodiment of this invention can offer a more accurate lie detector than currently available on the market, working in a way different than the common use polygraph. There is no need for cooperation, or for asking questions and getting answers from the tested person. An embodiment of this invention comprises the method of presenting the tested person with certain auditory stimuli, recording the person's brain response to these stimuli, and determining which of the stimuli are meaningful to the person, and what is his or her personal emotional meaning of these stimuli.
7. BCI (brain computer interface) for home consumers for gaming and self development—
    Our tool can serve as BCI, by identifying what the user wants or desires out of a list of objects. The user can thus control a game or software for self improvement or for other use. The tool can also identify a desired option, even if subconsciously out of a list of options or choices. The tool can also discriminate personal positive from personal negative.
8. People after stroke
    It is possible to use an embodiment of this invention for people after stroke in several ways—
    (1) Applying the method to people after stroke before any therapy. A database of BAP (including patterns and electrode combinations) to a given list of words will be built. A similar database of BAP to the same list of words will be created after therapy, to monitor the effect of therapy and divide the participants in therapy to good responders to therapy and less good responders to therapy. The BAP of each group will be used in further examinations to predict the response of patients to therapy. A similar therapy assessment can be carried for different groups of patients.
    (2) Using a database as described here, the personal meaning of words to a person
    can be determined (what the individual wishes for, etc.), even if the person cannot well communicate, such as may be after stroke.

9. Drug choice and diagnosis for psychiatry
   1. Apply electrodes at designated localizations according to electrode combinations database, and according to the desired information to be recorded.
   2. Record EEG.
   3. Connect patients to headphones or earphones, and apply auditory verbal stimuli words and first names of familiar close people and unfamiliar people, with similar phonetics across all stimuli, while recording EEG.
   4. Repeat each stimulus at least once.
   5. Do basic EEG analysis to ERP, as described herein.
   6. or Analyze EEG gamma band.
   7. Identify BAP in response to selected stimuli, for example familiar and unfamiliar, or personal-emotional and neutral.
   8. Compare the BAP received to BAP from a given database (an example
   of such a database is included herein). Different BAP may be present in the database for different groups of disorders.
   9. Run a statistical test to find to which BAP group the received BAP are the more similar.
      (1) Based on the group of known BAP that was selected as similar to the received BAP, a diagnosis may be suggested based on the diagnosis that is related to this known group of BAP.
      (2) An additional database of diagnoses for each group of BAP can be included or developed.
   10. A drug of choice may be suggested, based on the chosen group of BAP.
   11. The analysis may be run again (steps 1 to 11) after a selected drug was administered, to assess the effect of the drug on the BAP, and help make the decision if this drug is the right drug for this patient. If the BAP have changed (to be normal), than the drug is assumed to be the right one.
10. Child psychology and psychotherapy: a choice of stimuli which are related to a past traumatic event, or stimuli that are personal-emotional to the child, in order to focus the treatment or for forensic use.
   (1) Interview parents or therapist to collect first names of familiar people children, care givers, other workers and family.
   (2) Prepare also a list of words relevant to the life cycle and experiences of the child, or words suspected to be related to a previous trauma.
   (3) Add similar control stimuli with similar physical properties (beginning with similar consonants, similar duration of stimulus).
   (4) Prepare stimuli for administration—prepare audio files of stimuli on computer.
   (5) Connect to EEG channels.
   (6) Record EEG while child is exposed to a number of repetitions of stimuli, with at
   least one repetition.
   (7) Do basic EEG (ERP) analysis, as described herein
   (8) Identify BAP.
   (9) Compare to database of BAP.
   (10) For auditory stimuli, response to personal-emotional stimuli may include one or more of the following increased amplitude of P1, N1 or P2; prominent P3, Late positive component, frontal shift, or N400.
   (11) If at least one of the above is present, than suspect individual importance (II) to the subject, or that the stimulus is related to traumatic event.
   (12) It is also possible to compare to the database of subjective positive subjective negative brain areas (brain areas in response to positive or negative stimuli).
   (13) Choose stimuli that are relevant to traumatic experience.
   (14) Build output: which are the relevant stimuli. The output will be delivered to the therapist in order to focus the therapy, or for forensic use.
11. Psychotherapy
   Out of a given list of words and stimuli, pick words which are personal-emotional, or related to a past trauma.
   1. The words will be chosen as related to past trauma, based on a comparison of the evoked BAP to BAP from a given database, such as described herein.
   2. The chosen words will be used to focus the treatment (psychotherapy), or determine the target of cognitive psychotherapy to the specific traumatic event.
12. Identification of personal-emotional and trauma related names (for child psychology and psychotherapy) The goal of this application is to identify first names of people that are important to the child, or people that are related to traumatic experience that the child had. The method is the following.
   (1) Interview parents to collect first names of people that the child is familiar with.
   (2) Add to the list of names neutral names of people (not significant to the child) with similar physical and phonetic properties.
   (3) Record auditory names on computer and save as audio files or select names from a given database of recorded names.
   (4) Connect the child to EEG while the child is exposed to the names (it is
   possible to use a modified paradigm, with facial pictures instead of first names)
   (5) Analyze the EEG signals to receive ERP and gamma band.
   (6) Compare the received signals to a database of ERP components and related
   meanings, such as that is included herein.
   (7) Identify the names that are relevant to traumatic experience, using a database of ERP components and electrode combinations.
13. Identification of personal-emotional and trauma related words (for child psychology
   and psychotherapy)
   Goal of the application: to identify words that are related to a traumatic experience in the past.
   (1) Choose and prepare a general words list covering fields that are related to the child life and daily experiences.
   (2) Add assumed neutral words (not describing the child experiences; for example "mother" can be assumed as significant, "leaf" may assumed to be neutral; the final personal meaning of the included words will be determined by the ERP test), with similar physical properties.
   (3) Record words, or select words from a given database of recorded auditory words.
   (4) Administer auditory words stimuli while the child is connected to EEG channels recording EEG.
   (5) Analyze the ERP, basic analysis is described herein.
   (6) Compare the ERP patterns to a database of such as included herein.

(7) Select and identify words that are related to trauma, based on the ERP received patterns.
(8) Diagnose if there was a traumatic experience.
(9) Diagnose which words and persons are related to the traumatic experience.
(10) For forensic use: identify who has hurt the child in what way.

11. Database of Patterns

The illustrated database was established on the study of patterns in English speaking healthy adults, in the ages of 20-76, both males and females. This database may be adapted in the future to include individuals with different disorders, or to include people with other distinct characteristics, such as people from different cultures, or different ages, such as children or babies. The basic principles of this database stay the same then. The principle of this database is that there are specific response patterns, present in EEG (Electro-Encephalo-grapy) or ERP (event related potentials), that carry a specific personal meaning across people, such as true, or ultimate, passion. For a certain auditory stimulus connected to a certain personal meaning, one or more of the patterns associated with this meaning may be present. If more patterns related to a specific personal meaning are present for a certain stimulus, than this stimulus is more likely to be connected to this personal meaning. The presence of specific patterns will be linked to the presence of specific meaning to the person, such as true, or ultimate, passion. The patterns described here specifically are related to (1) the presence of true, or ultimate, passion, (2) a negative or traumatic personal emotional meaning and (3) a positive personal emotional meaning, or to "like". The meanings that are mentioned here are personal meanings. The patterns described herein are for EEG recorded in response to auditory stimuli.

Comment 1: All the times listed here are latencies in milliseconds (ms), from stimulus onset.

Figure 5:
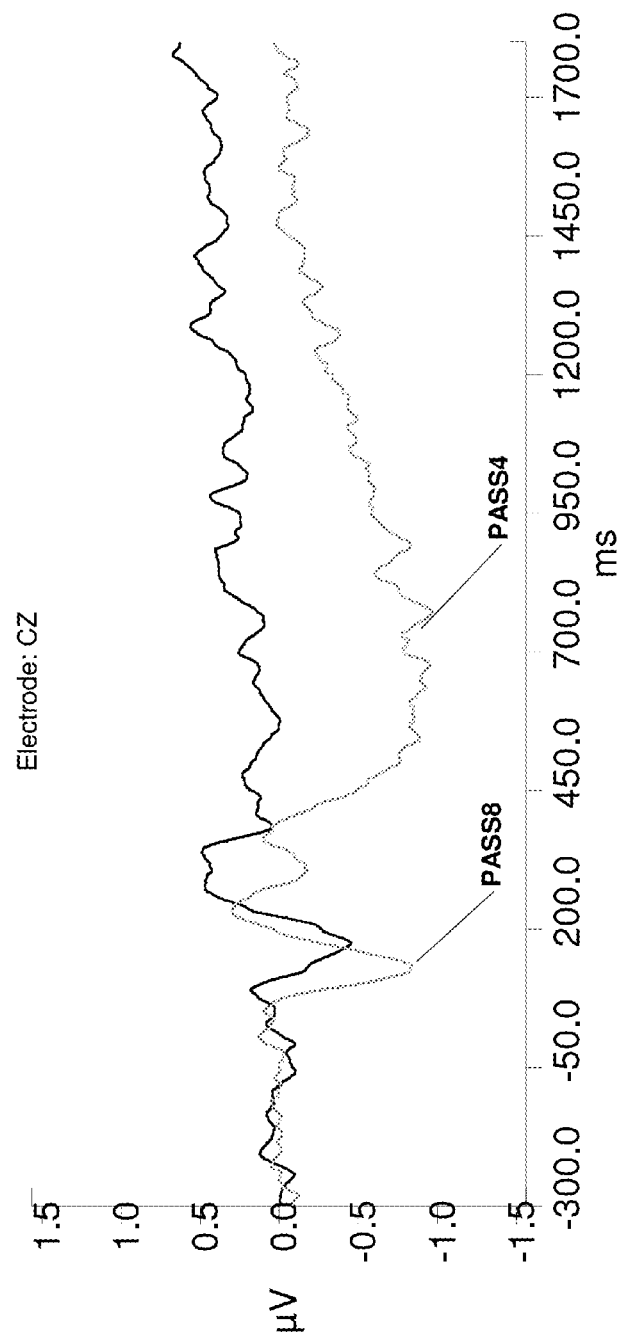
FIG. 5 schematically shows voltage detected in Electrode Cz vs. time.

Comment 2: All electrodes listed here are listed in the common names using the 10/20 system adapted for 64 channels. FIG. 5 shows the common locations of the electrodes on the scalp.

Comment 3: The components or peaks mentioned by name are the standard ERP components, especially for auditory stimuli: P2 being the second prominent positive peak from the stimulus onset, P1 the first prominent positive peak, N1 the first prominent negative peak, P3 is the third prominent positive peak. etc. N400 is the negative peak in frontal locations around the time of 400-500 ms after stimulus onset. Auditory P1, N1, P2 and P3 are explained for example in—Martin B A, Tremblay K L, Korczak P. Speech Evoked Potentials: From the Laboratory to the Clinic. Ear Hear. 2008; 29(3):285-313; Wunderlich J L, Cone-Wesson B K, Maturation of CAEP in infants and children: A review. Hearing Research 2006; 212(1-2):212-23.

Comment 4: The components or peaks mentioned here by name are for auditory stimuli. Comment 5: We measured up till 1800 ms post stimulus, some of the shifts described here may be present and measured at later times.

Comment 6: The figures that are attached here, are only examples that we have measured, of the general patterns such as described here.

Comment 7: The electrodes mentioned here are the common electrodes names from the 10/20 system (with adaptation to 64 channels). Other electrodes' systems may be used. For each pattern, the relevant area is mentioned, in which the relevant electrodes are to be found.

Comment 8: In order to obtain the patterns described here, auditory words, similar to all participants were used. For each participant, 3 words that were related to a certain personal meaning were chosen. The number of repetitions used here was about 70 per word.

Comment 9: A pattern may be present in one or more of the electrodes mentioned here, if a pattern for a certain stimulus is present in more electrodes than for other stimuli in the same person, than this stimulus is more associated to that personal meaning which is associated with this pattern.

Comment 10: 'Similar electrodes' here denotes electrodes having similar location over the scalp to the ones mentioned for a specific pattern, in any electrode system similar or different to the one used here.

Comment 11: For some of the patterns that are mentioned here, it is enough to measure the response to one stimulus. For other patterns, such as POS8 and POS9, there is a need to compare the response to one stimulus or a group of stimuli to the response to other stimuli in the same person.

Comment 12: For a certain personal meaning, for a certain stimulus, several patterns may be present. Some of the patterns overlap across different personal meanings. The presence of a certain cluster of patterns will direct to the personal meaning of a certain stimulus. The more patterns are present for that stimulus that are related to a specific personal meaning, the stronger the association of this stimulus to this personal meaning is.

Comment 13: If a pattern is present for more than one stimulus, than the stimulus to which the peak amplitude of this pattern is the greatest is more related to that personal meaning than the other stimuli for this person. A certain pattern may not appear at all times even when a stimulus is related to that personal meaning—other patterns may be present instead. If a certain pattern is present for a certain stimulus, than this stimulus is likely to have this personal meaning for that person. If it is not present, still other patterns related to that personal meaning may be present and the stimulus may still have that personal meaning.

With reference to the FIG. in general, in all of the FIG.: Light lines designate the response to stimuli related to "passion" for the examinee. Dark heavy lines designate the response to stimuli related to a negative personal emotional meaning, for the examinee. Light dashed lines designate the response to stimuli related to a positive personal emotional meaning, for the examinee. All the FIG. 2-24 are an average across several people. Notice different FIG. may have a slightly different voltage scale. The scale in each FIG. was chosen so that the whole signal would fit within the scale. FIG. 1 is a schematic drawing illustrating the positioning of all electrodes, according to the 10/20 positioning adapted for 64 electrodes.

Some of the embodiments include the following identified patterns:

A. Patterns Associated with "Passion" (PASS#)

When at least one of these described patterns is present for a certain stimulus, that stimulus is related to true, or ultimate, passion ("passion"). If a stimulus has several of these patterns present—the more patterns are present, the more this stimulus may be related to true, or ultimate, passion. A response can be measured to one stimulus alone, analyzed and processed to identify if one or more of these patterns are present, if so, this stimulus may be related to "passion", especially as defined herein.

1. Pattern PASS1: A prominent positive deflection having a maximal peak (occurring over the right hemisphere) within 100 ms after an auditory P2 (occurring over the frontal scalp locations). This component (deflection) is similar to the common measured auditory (frontal) P2, but is present mainly over the right hemisphere. It has a peak latency (latency of the maximal peak of the deflection) within 100 ms from the time of auditory P2 peak measured for that stimulus for that person. Regardless of the time of P2, this pattern will have a peak latency over the right hemisphere at a time between 200-500 ms. Auditory P2 is measured over frontal locations, such as ones recorded in electrodes Fz, FCz, or other frontal electrodes. This pattern is prominent over the right hemisphere and can be measured by C6, FT8 or T8 electrodes of the common 10/20 system adapted for 64 channels, or similar electrodes over the right hemisphere. This pattern is illustrated in FIG. 2,3,12.

If this pattern is present for more than one stimulus, than the stimulus to which the peak amplitude of this pattern is the greatest is more related to "passion", (or positive personal emotional meaning) than the other stimuli for this person. A description of an algorithm to identify the presence of this pattern is described herein, at the section "pattern recognition". This is a significant pattern indicative of the personal meaning of "passion" or positive personal emotional meaning connotation. Yet, it does not appear at all times even when a stimulus is related to "passion"—other patterns may be present instead. If this pattern is present for a certain stimulus, than this stimulus is likely to be connected to passion, or to have a positive personal emotional meaning for that person. If it is not present, still other patterns related to passion may be present and the stimulus may still be related to "passion".

This pattern is associated with both "passion" and a positive personal meaning, but it may have a slightly different scalp topography for those two personal meanings. Its peak amplitude is larger for a stimulus with a positive personal emotional meaning over right frontal-temporal locations (such as measured by electrode FT8). It may be measured on right central locations (such as measured by electrode C6) mainly if it is related to "passion", and not just general positive personal emotional meaning.

2. Pattern PASS2: A positive shift that appears anytime from 350 ms from stimulus onset till 1800 ms latency from stimulus onset or even later than that. It appears over the right hemisphere in a central or temporal location—and can be measured by C6, or a similar electrode. This pattern may be prominent over the right temporal and parietal scalp locations—thus measured also by electrodes such as FT8, T8, TP8 and P8. This pattern is illustrated in FIG. 2.

Figure 4:
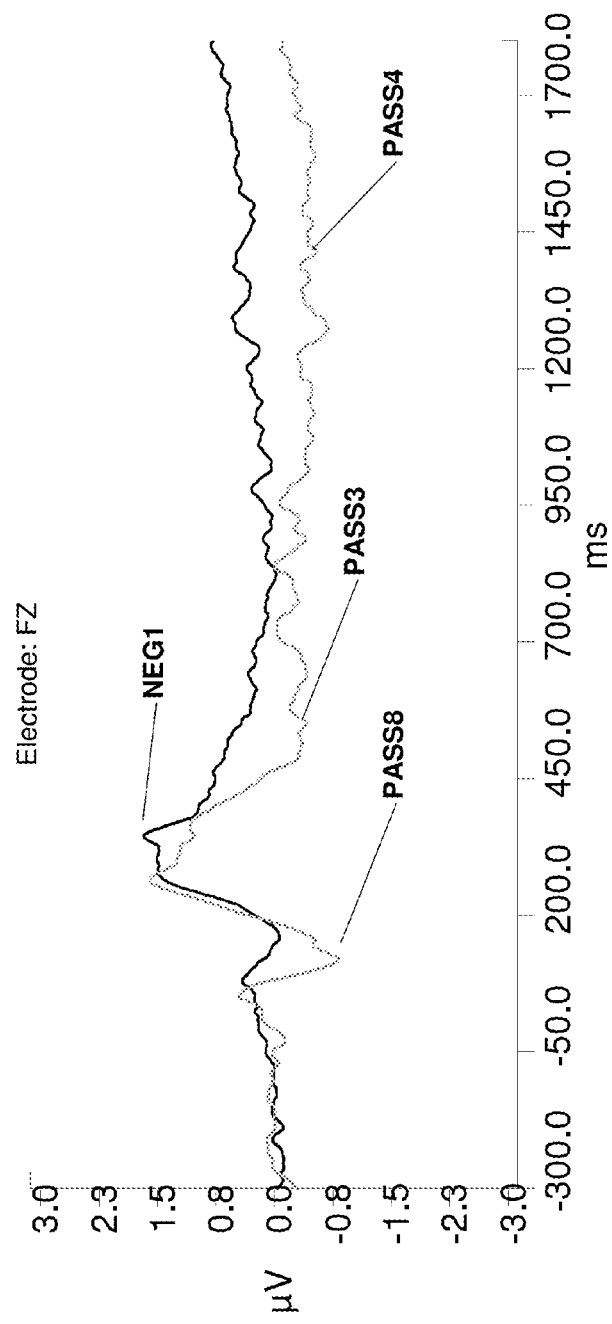
FIG. 4 schematically shows voltage detected in Electrode Fz vs. time.

3. Pattern PASS3: A prominent Negative deflection with a minimum peak. This pattern is somewhat similar to the common frontal N400. It appears anytime after at least 100 ms after the peak latency of an auditory N1 measured in the same person to the same stimulus. This component may be prominent over frontal and central locations, especially over the right hemisphere. It can be measured by FCz, FC2, FC4 or similar electrodes. This pattern is illustrated in FIG. 4.

4. Pattern PASS4: A negative shift that starts anytime from 350 ms onwards, which may last till 1800 ms or later. This negative shift is prominent especially over frontal and central locations, especially over the right hemisphere, and can be measured by electrodes such as FPZ, FP2, FP1, FC4, FCZ, CZ, CPz, CP2 or similar electrodes. This pattern is illustrated in FIG. 4, 5.

Figure 6:
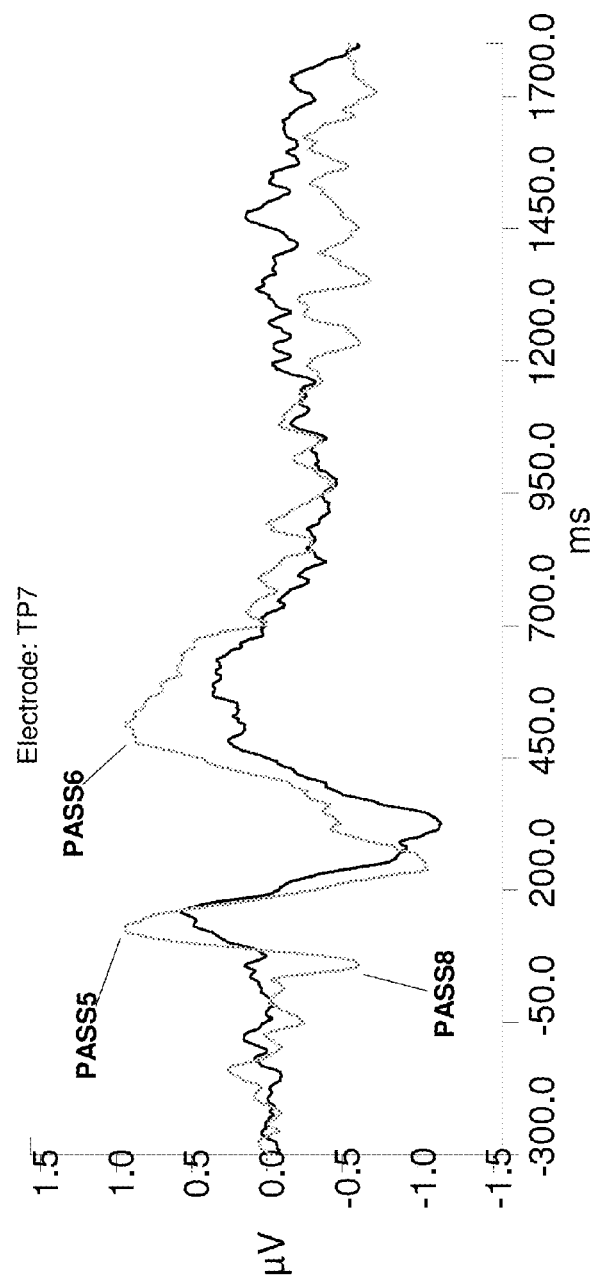
FIG. 6 schematically shows voltage detected in Electrode TP7 vs. time.

5. Pattern PASS5: Increased amplitude of a positive peak, such as part of the common auditory response P1-N1-P2 anytime between 50 ms to 350 ms, in frontal, temporal, central or occipital locations. This pattern can be measured by electrodes such as FCz, FC3, Cz, CP2, FC4, TP7, CP5, FT7, O2 or similar electrodes. When the response to several stimuli is recorded in one person, than the peak amplitude of some of the peaks between 50-350 ms will be enlarged for stimuli related to "passion", when compared to the same peaks at similar latencies measured for other stimuli not related to "passion" in the same person. This pattern is illustrated in FIG. 6,7,22.

6. Pattern PASSE: A positive deflection having a maximum peak between 200 ms to 1000 ms or later. This pattern may seem similar to the common measured P3, but has different scalp topography. This pattern is prominent over the left hemisphere including frontal, central, temporal and parietal areas. This pattern may be measured by electrodes such as C5, P7, P5, TP7, FT7, CP5, POZ, PO3, Oz, or similar electrodes. This pattern is illustrated in FIG. 6,16,20.

Figure 7:
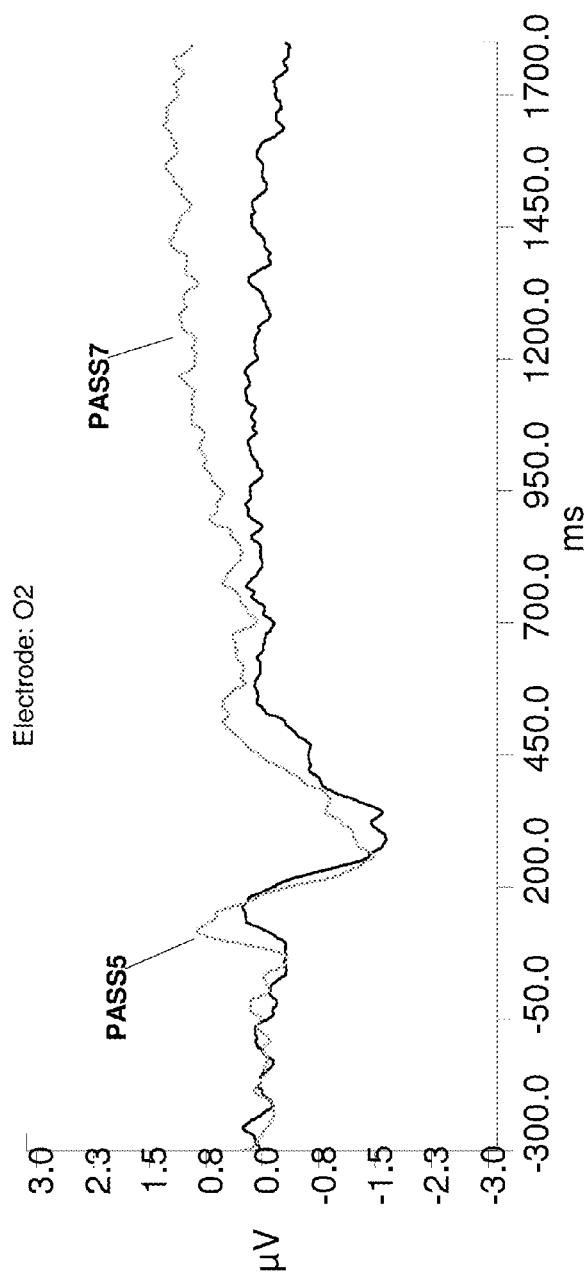
FIG. 7 schematically shows voltage detected in Electrode O2 vs. time.

7. Pattern PASS7: A positive shift, that starts anytime from 300 ms till 1800 ms or later. It may appear over parietal or occipital scalp locations, and can be measured by electrodes such as 02, T7, or similar electrodes. This pattern is illustrated in FIG. 7.

8. Pattern PASSE: Increased amplitude of a negative peak, that appears at a time between 150-350 ms from stimulus onset. This pattern is related mainly to the auditory N1. This negative peak may appear for several stimuli measured in the same person, but its amplitude is enlarged for stimuli that are related to "passion" compared to other stimuli measured in the same person; it is enlarged over the right hemisphere or in the midline, over frontal, temporal, parietal or occipital areas. It can be measured by electrodes such as FPz, FP2, Fz, FC4, Cz, CP2, Oz, POz, FTE, or similar electrodes. Occasionally it can be measured over the left hemisphere, such as by electrodes TP7 or similar electrodes. This pattern is illustrated in FIG. 4,5,13,18,19.

Figure 8:
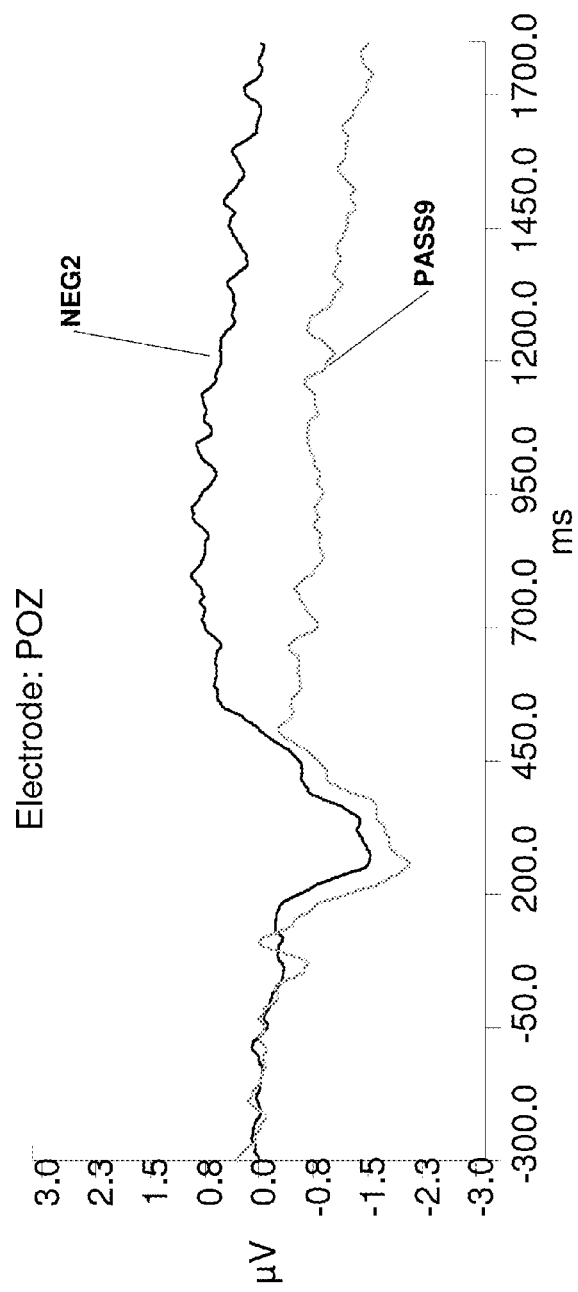
FIG. 8 schematically shows voltage detected in Electrode POz vs. time.

9. Pattern PASS9: A negative shift over the parietal or occipital regions that starts as early as 350 ms and may last till 1800 ms or later. This pattern can be measured by POz or similar electrodes. This pattern is illustrated in FIG. 8.

Figure 9:
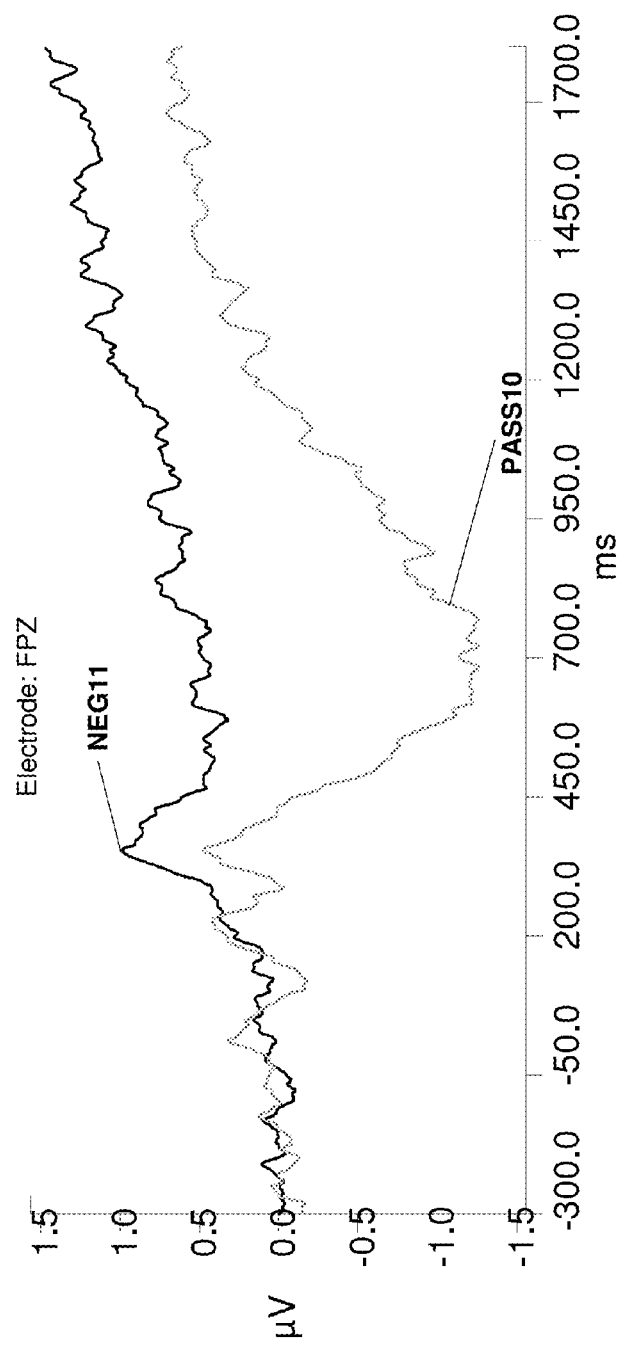
FIG. 9 schematically shows voltage detected in Electrode FPz vs. time.

10. Pattern PASS 10: A prominent negative deflection with a minimum peak present over frontal locations with minimum peak latency between 400 ms to 1000 ms post-stimulus onset. This pattern may be measured by electrodes such as FPz, FP1, FP2, or similar electrodes. This pattern is illustrated in FIG. 9.

11. Additional patterns may be present as part of the patterns associated with "passion".

B. Patterns Associated with a Negative Personal Emotional Meaning of the Stimulus (NEG#)

Negative personal emotional meaning may also be related to the following personal meanings: Somebody that the tested person does not like, something that the tested person does not like or a stimulus related to a bad, or traumatic memory, or some other negative personal emotional meaning.

1. Pattern NEG1: A delayed peak latency of some peak appearing between 50-500 ms latency, while compared to the a similar peak appearing for other stimuli in that person. This pattern is prominent mainly for the auditory ERP peak P2.

This pattern may be present also for the other auditory ERP peaks P1 and N1. This pattern of delayed peak latency appears over the midline and right hemisphere, including frontal, central and parietal locations, and can be measured by electrodes such as F2, Fz, FCz, F4, FT8, C4, Cz, C2, FC4, PO8, PO6, P8 or similar electrodes. This pattern is illustrated in FIG. 4,10.

2. Pattern NEG2: A positive shift that starts from 450 ms or later and may last till 1800 ms or later, that appears over parietal or occipital locations and can be measured by electrodes such as CPz, POz or similar electrodes. This pattern is illustrated in FIG. 8.

Figure 11:
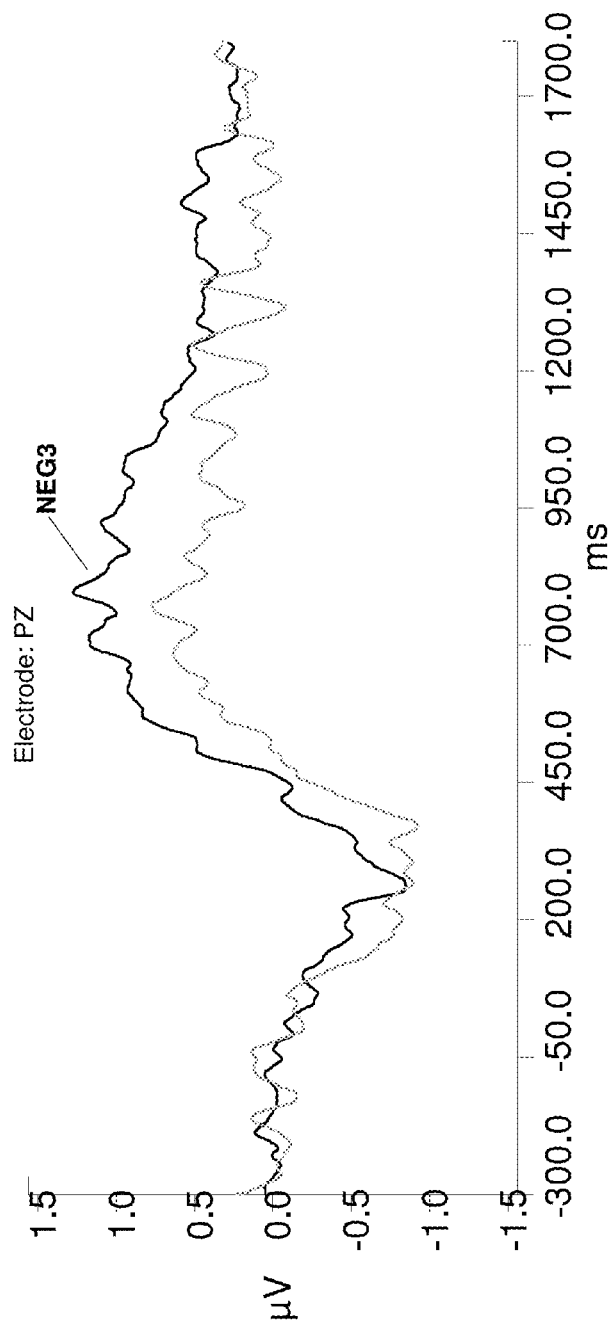
FIG. 11 schematically shows voltage detected in Electrode Pz vs. time.
Figure 12:
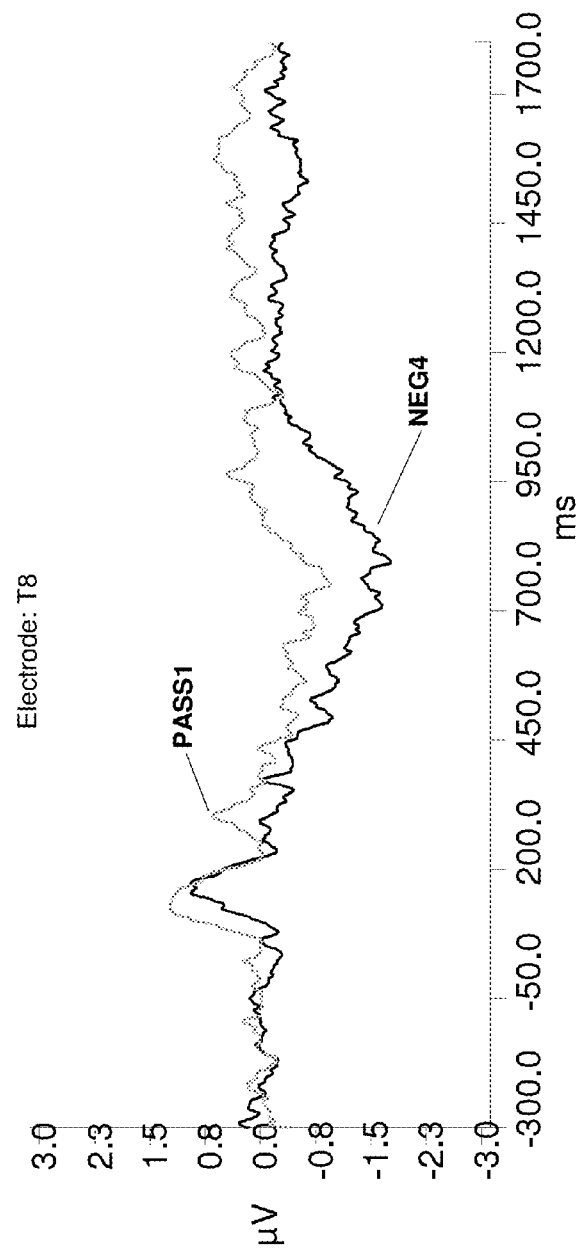
FIG. 12 schematically shows voltage detected in Electrode T8 vs. time.

3. Pattern NEG3: A positive deflection having a maximum peak at a time between 400-1200 ms over parietal locations. This pattern is similar to the common measured P3. It can be measured by any electrode in parietal scalp locations, such as P1, P2, P3, Pz, CP1, CP2, CP4 or similar electrodes. This pattern is similar to POS3, but the peak amplitude of POS3, associated with positive personal emotional meaning, may be greater than that of NEG3, associated with negative personal emotional meaning. This pattern is illustrated in FIG. 11,13.

4. Pattern NEG4: A negative deflection with peak amplitude between 500 to 900 ms appearing over the right hemisphere in frontal or temporal locations. This pattern can be measured by electrodes F8, FT8, T8 or similar electrodes, and may be occasionally measured also by C6 or similar electrodes. NEG4 is similar to POS2, but POS2, appearing for stimuli with positive personal emotional meaning, has a shorter peak latency and larger peak amplitude than NEG4, appearing for stimuli with a negative personal emotional meaning. The peak latency of NEG4 may be around 800 ms, compared to the peak latency of POS2 which is usually around 700 ms. But, in different people these latencies may be between 500-900 ms. This pattern is illustrated in FIG. 2,3,12.

5. Pattern NEG5: A negative shift that starts from 500 ms or later and may last till 1800 ms or later, over the right hemisphere in frontal or central locations, that can be measured by electrodes F6, FC6, C6, or similar electrodes. This pattern is more specific to stimuli with negative personal emotional meaning especially when measured over right frontal locations, such as measured by F6 or similar electrodes. This pattern is illustrated in FIG. 2.

Figure 13:
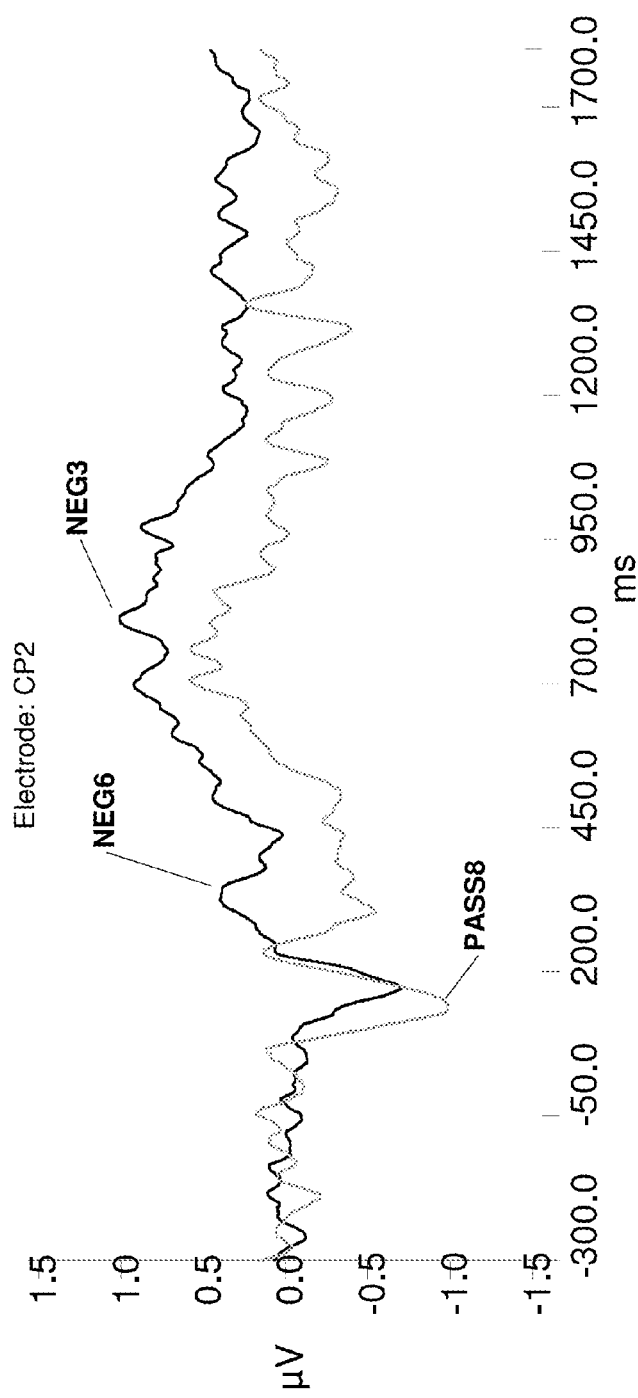
FIG. 13 schematically shows voltage detected in Electrode CP2 vs. time.

6. Pattern NEG6: A positive deflection with a maximum peak at a latency between 200-500 ms over the right hemisphere in central or parietal locations, that can be measured by electrodes such as CP2, CP4, Cz or similar electrodes. This pattern peak latency occurs after the peak latency of an auditory P2 measured at the same person for the same stimulus over frontal locations, such as by electrodes Fz, FCz or similar electrodes. This pattern is illustrated in FIG. 13.

Figure 10:
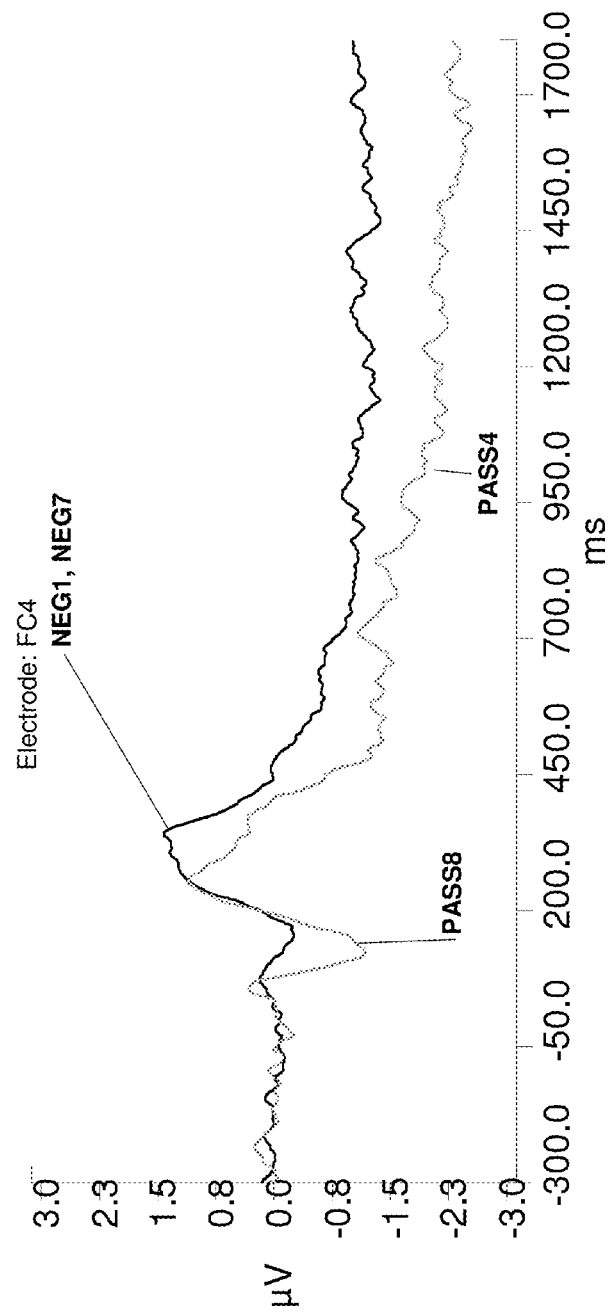
FIG. 10 schematically shows voltage detected in Electrode FC4 vs. time.

7. Pattern NEG7: Increased amplitude of a positive peak with a peak latency between 200-500 ms, which is similar to the auditory P2. This pattern of increased amplitude is in comparison with a similar peak (which is similar to auditory P2) amplitude measured for other stimuli in the same person in the same electrode. This pattern of increased amplitude is present over the right hemisphere and midline on frontal and central locations, and can be measured by electrodes such as Cz, C2, FC4 or similar electrodes. This pattern is illustrated in FIG. 10.

Figure 14:
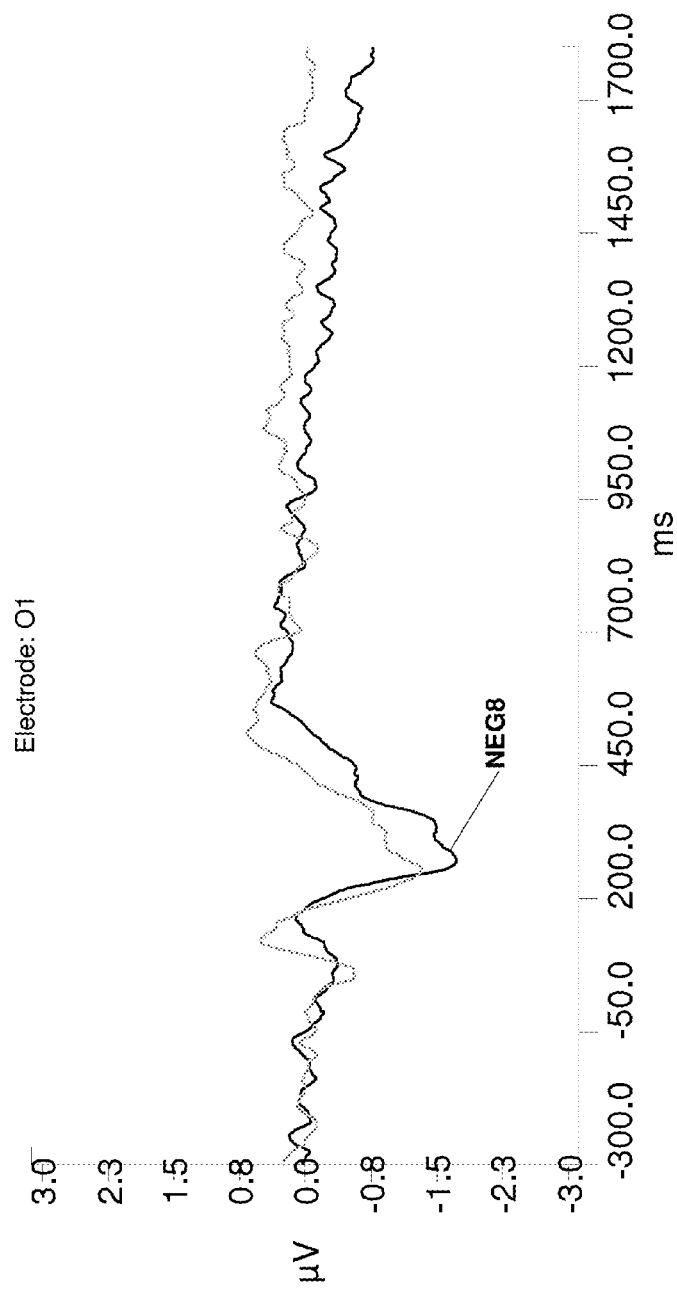
FIG. 14 schematically shows voltage detected in Electrode O1 vs. time.

8. Pattern NEG8: Increased amplitude of a negative peak with a peak latency between 200-500 ms. This increased amplitude of that peak is present over parietal or occipital scalp locations and can be measured by electrodes such as P3, PO7, PO3, P1, O1, Oz, O2 or similar electrodes. This pattern is illustrated in FIG. 14.

Figure 15:
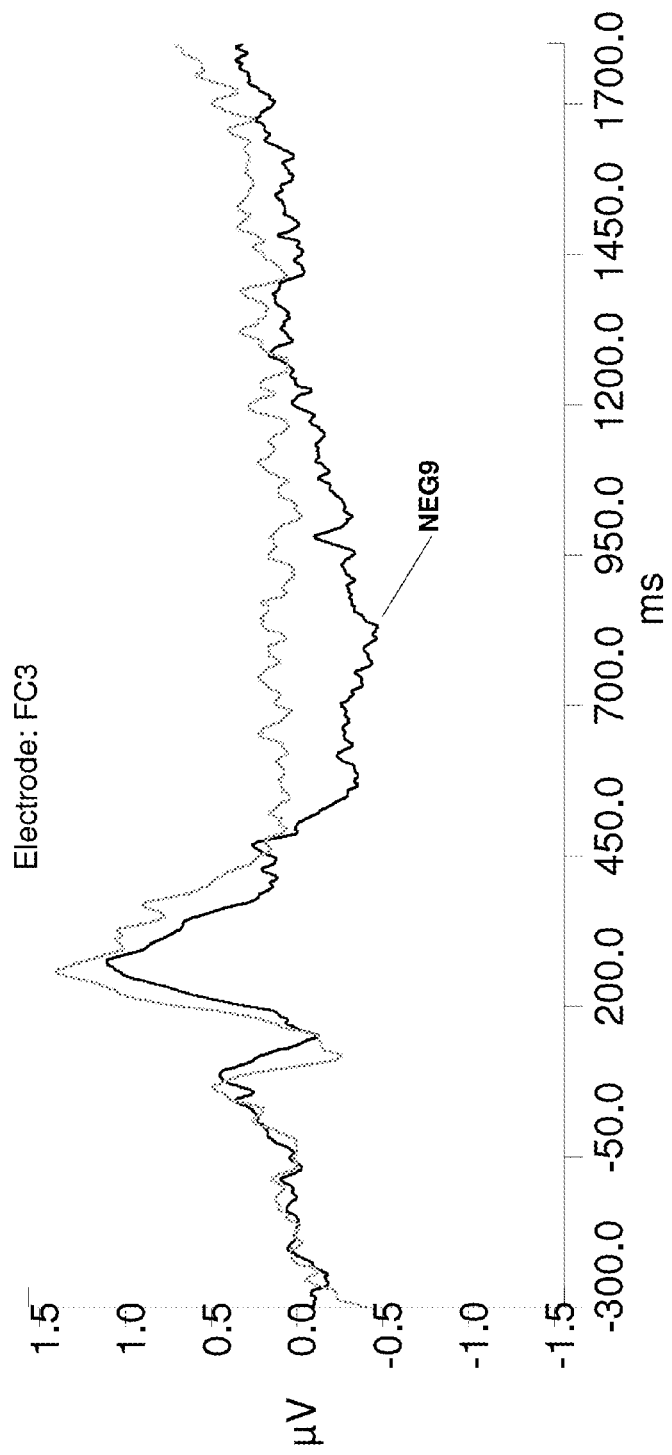
FIG. 15 schematically shows voltage detected in Electrode FC3 vs. time.

9. Pattern NEG9: A negative shift that starts from 400 ms or after that and may last till 1800 ms or later, over the left hemisphere in central, frontal and frontal-temporal locations, that can be measured by FC3, C3, C1, FC1, FT7, FC5 or similar electrodes. This pattern is illustrated in FIG. 15,16.

Figure 16:
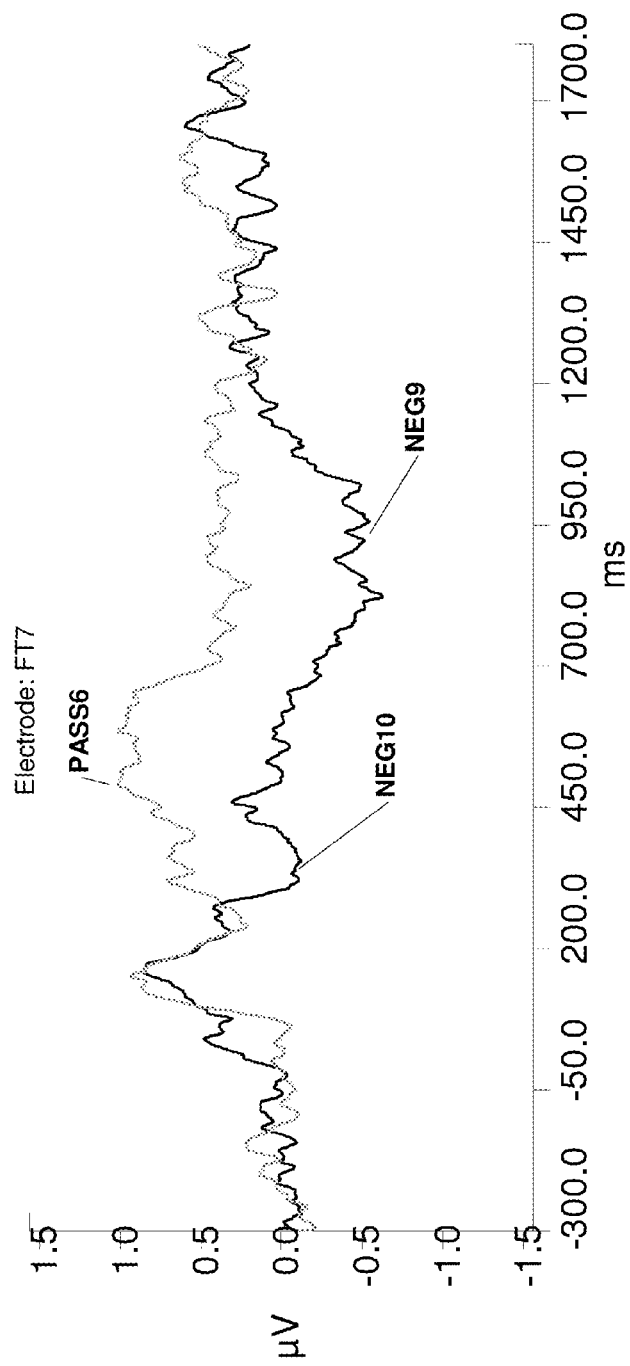
FIG. 16 schematically shows voltage detected in Electrode FT7 vs. time.

10. Pattern NEG10: A negative deflection having a minimum peak between 200-500 ms over the left hemisphere at temporal locations, and can be measured by electrodes TP7, FT7, or similar electrodes. This pattern is illustrated in FIG. 16.

11. Pattern NEG11: A positive deflection with a maximum peak at latency of 250-500 ms over frontal scalp locations, such as measured by FP1, FP2, FPz or similar electrodes. This pattern is somewhat similar to POS10, but has an earlier peak latency (may be before 500 ms), and the deflection ends earlier for NEG11 compared to POS10. This pattern is illustrated in FIG. 9.

12. Additional patterns may be present and part the patterns associated with negative personal emotional meaning.

C. Patterns Associated with a Positive Personal Emotional Meaning of the Stimulus (POS#)

Positive connotation of the stimulus may denote also the following personal meanings: somebody or something that the person loves, likes, or cares about, or a stimulus related to a good memory from the past, or some other positive personal emotional meaning.

1. Pattern POS1: A prominent positive deflection having a maximal peak (occurring over the right hemisphere) within 100 ms after an auditory P2 (occurring over the frontal scalp locations). This component (deflection) is similar to the common measured auditory (frontal) P2, but is present mainly over the right hemisphere. It has peak latency (latency of the maximal peak of the deflection) within 100 ms from the time of auditory P2 peak measured for that stimulus for that person. Regardless of the time of P2, this pattern may have a peak latency over the right hemisphere at a time between 200-500 ms. Auditory P2 is measured over frontal locations, such as ones recorded in electrodes Fz, FCz, or other frontal electrodes. This pattern is prominent over the right hemisphere and can be measured by F8, T8 or FT8 electrodes of the common 10/20 system, or similar electrodes over the right hemisphere. Its scalp topography may be slightly different than that of the similar pattern PASS1, having peak amplitude over the right frontal-temporal scalp, thus measured by F8, T8, FT8 but not so much by right central electrodes such as C6.

If this pattern is present for more than one stimulus, than the stimulus to which the peak amplitude of this pattern is the greatest is more related to positive personal emotional meaning than the other stimuli for this person. A description of an algorithm to identify the presence of this pattern is described herein, at the section "pattern recognition". This is a significant pattern indicative of the positive personal emotional meaning. Yet, it does not appear at all times even when a stimulus is related to positive personal emotional meaning—other patterns may be present instead. If this pattern is present for a certain stimulus, than this stimulus is likely to have positive personal emotional meaning for that person. If it is not present, still other patterns related to positive personal emotional meaning may be present and the stimulus may still have positive personal emotional meaning.

Figure 17:
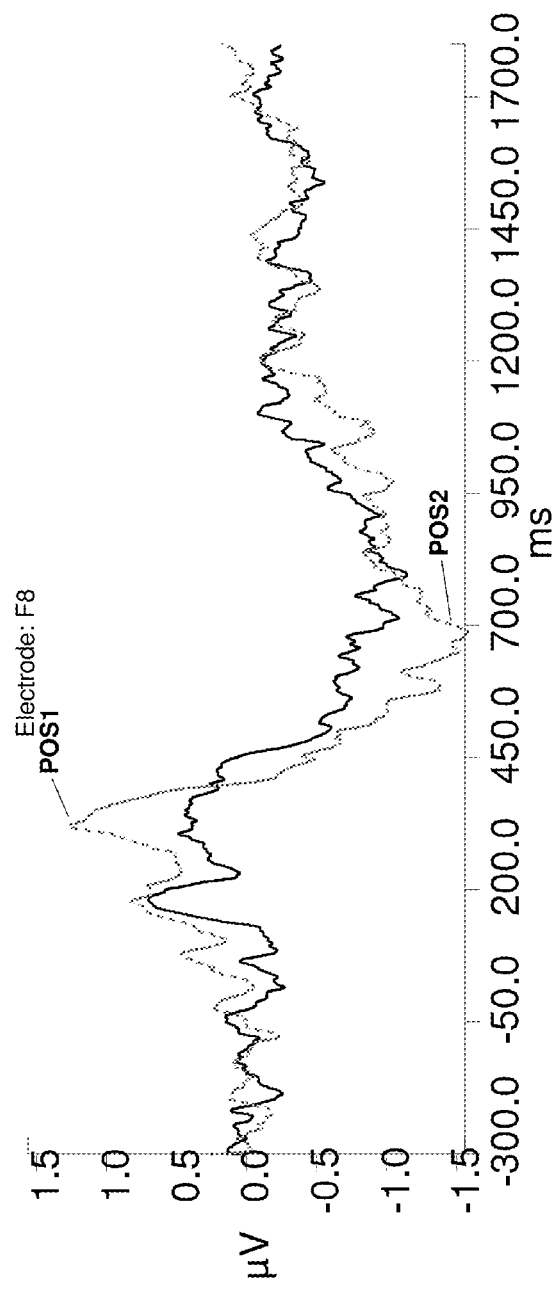
FIG. 17 schematically shows voltage detected in Electrode F8 vs. time.

A similar pattern is associated with both "passion" and with positive personal emotional meaning. Its peak amplitude is larger for a stimulus with a positive personal emotional meaning over right frontal temporal locations (FT8 or a similar electrode). This pattern (POS1) is illustrated in FIG. 17.

2. Pattern POS2: A negative deflection with peak amplitude with latency between 500 to 900 ms appearing over the right frontal and temporal locations. This pattern can be measured by the electrodes F8, FT8, T8 or similar electrodes, and may be occasionally measured also by C6 or similar electrodes. A similar pattern—NEG4—may be present for stimuli with negative personal emotional meaning, but the peak latency of POS2 for stimuli with positive personal emotional meaning may be shorter (such as about 700 ms) and the peak amplitude of POS2 may be larger than for NEG4. This pattern (POS2) is illustrated in FIG. 17.

Figure 18:
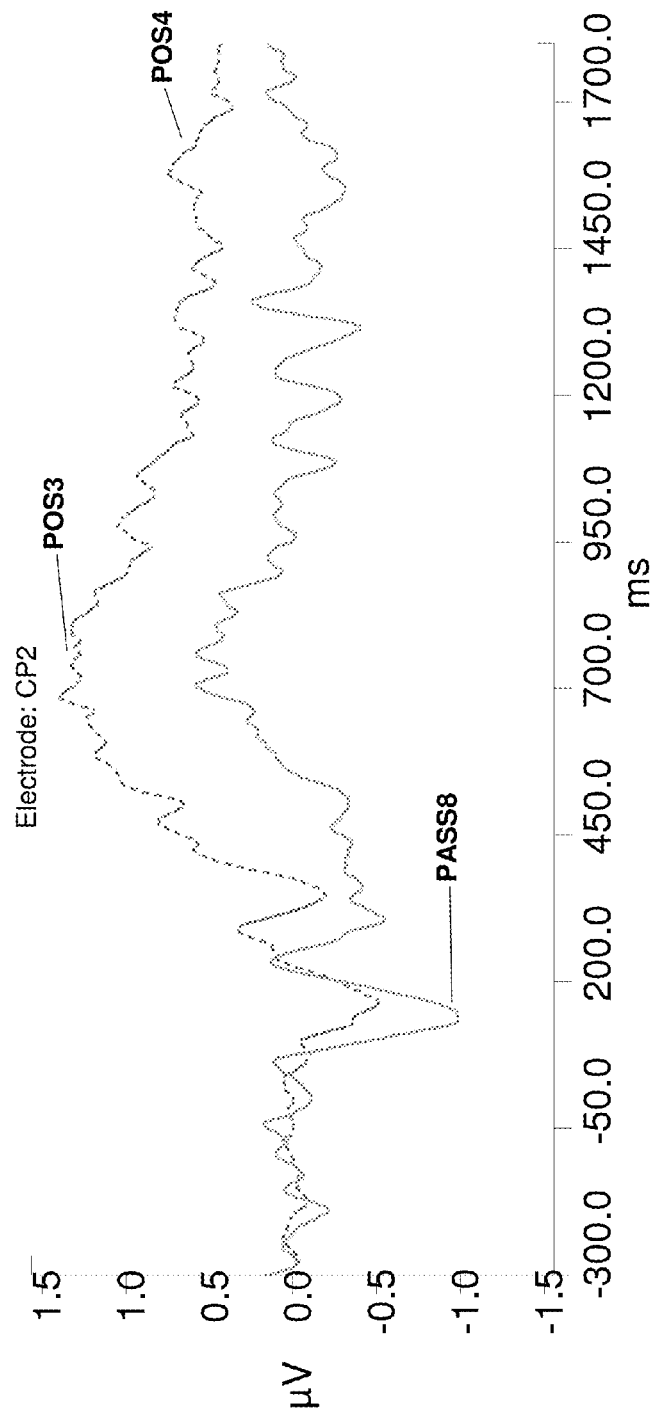
FIG. 18 schematically shows voltage detected in Electrode CP2 vs. time.
Figure 19:
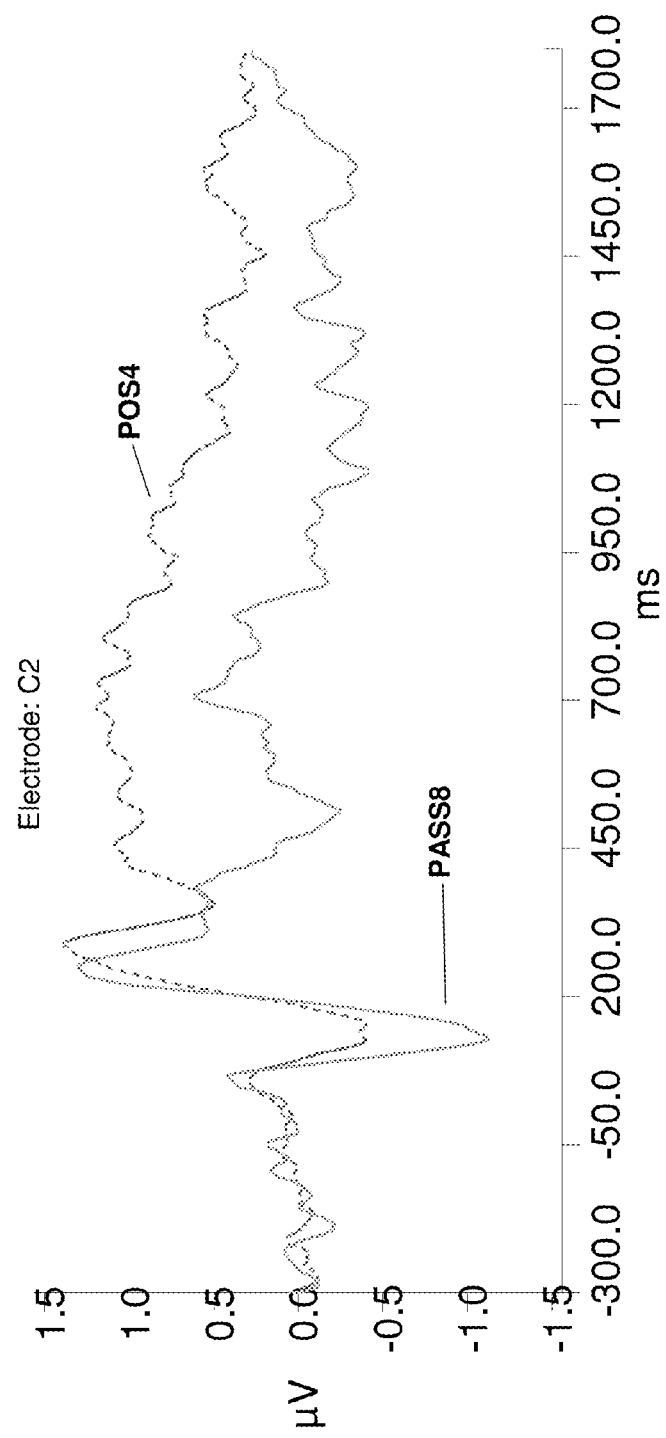
FIG. 19 schematically shows voltage detected in Electrode C2 vs. time.

3. Pattern POS3: A positive deflection having a maximum peak at a time between 400-1200 ms over parietal locations. This pattern is similar to the common measured P3. It can be measured by any electrode in parietal scalp locations, such as P1, P2, P3, Pz, CP1, CP2, CP4 or similar electrodes. A similar pattern may be present for negative personal emotional meaning, but the peak amplitude of this pattern (POS3) will be greater for stimuli with positive personal emotional meaning. This pattern (POS3) is illustrated in FIG. 18.

4. Pattern POS4: A positive shift that starts from 350 ms or later, and may last till 1800 ms or later. This positive shift appears over the right hemisphere and on the midline, in central and parietal locations, measured by electrodes such as C2, CP2, P2, C4, or similar electrodes. It may be measured occasionally on the left parietal scalp, such as by electrodes P1 or similar electrodes. Similar pattern of a positive shift in similar scalp locations may be measured for stimuli with negative personal emotional meaning, but than its amplitude is reduced compared to stimuli with positive personal emotional meaning. This pattern (POS4) is illustrated in FIG. 18,19.

Figure 20:
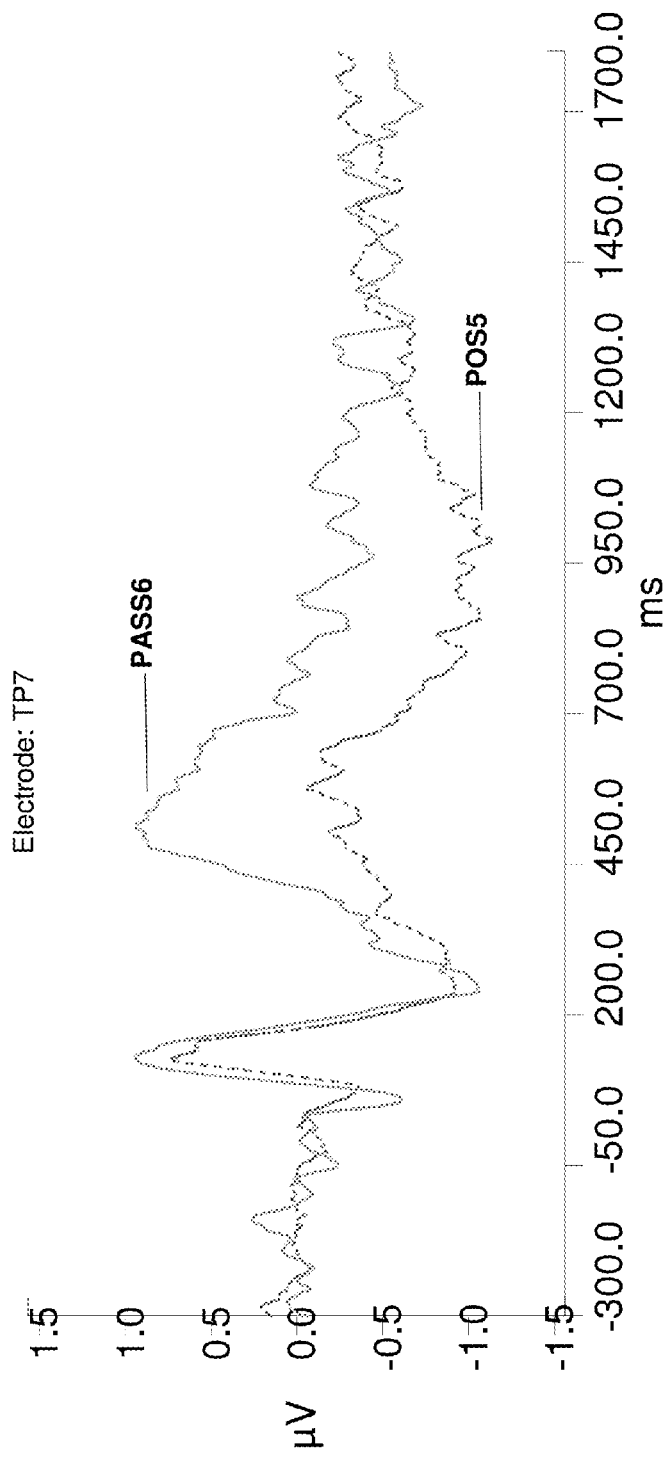
FIG. 20 schematically shows voltage detected in Electrode TP7 vs. time.

5. Pattern POS5: A negative shift that starts from 400 ms or later, and may last till 1800 ms or later. It appears over the left hemisphere, in frontal, temporal and parietal locations, and can be measured by electrodes such as FT7, TP7, FC5 or similar electrodes. This pattern is illustrated in FIG. 20.

Figure 21:
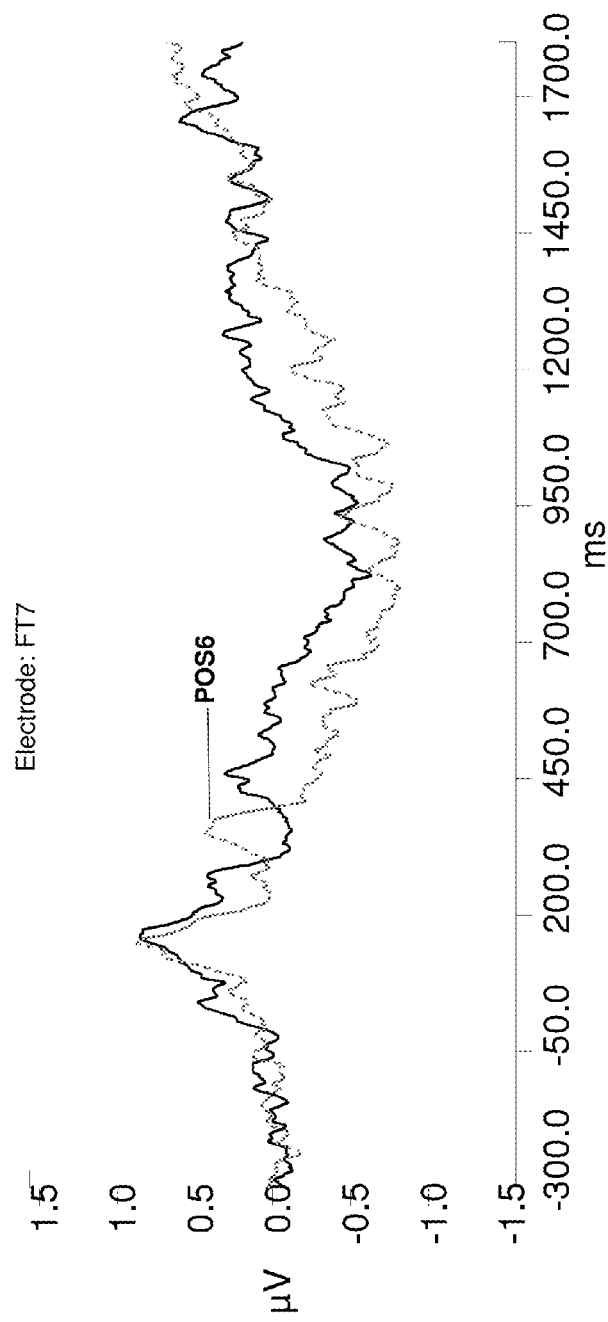
FIG. 21 schematically shows voltage detected in Electrode FT7 vs. time.

6. Pattern POSE: A positive deflection having a maximum peak at a latency of 200-500 ms over the left frontal-temporal scalp locations, and can be measured by electrodes such as FC5, FT7 or similar electrodes. This pattern is illustrated in FIG. 21.

Figure 22:
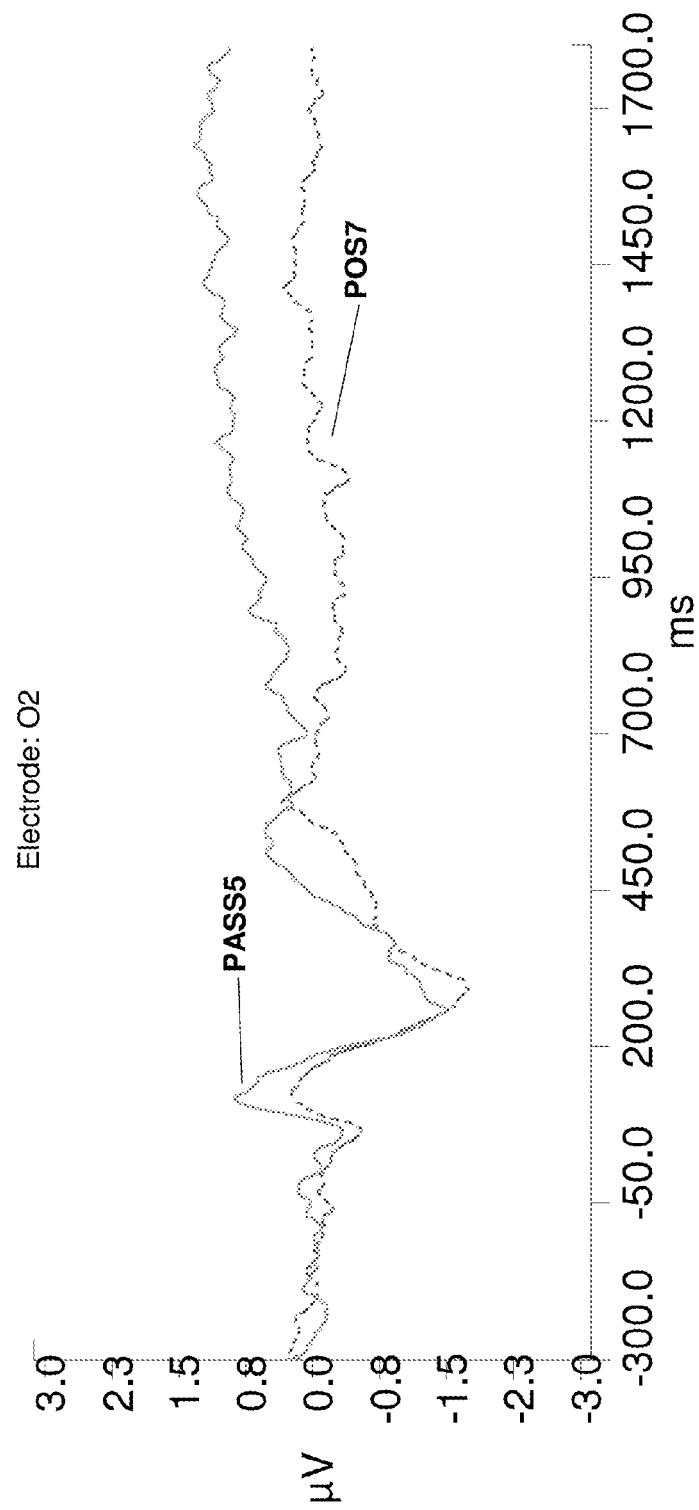
FIG. 22 schematically shows voltage detected in Electrode O2 vs. time.

7. Pattern POST: A negative shift, appearing at 600 ms or later that may last till 1800 ms or later, over occipital locations, and may be measured by electrodes such as Oz, O2, or similar electrodes. This pattern is illustrated in FIG. 22.

Figure 23:
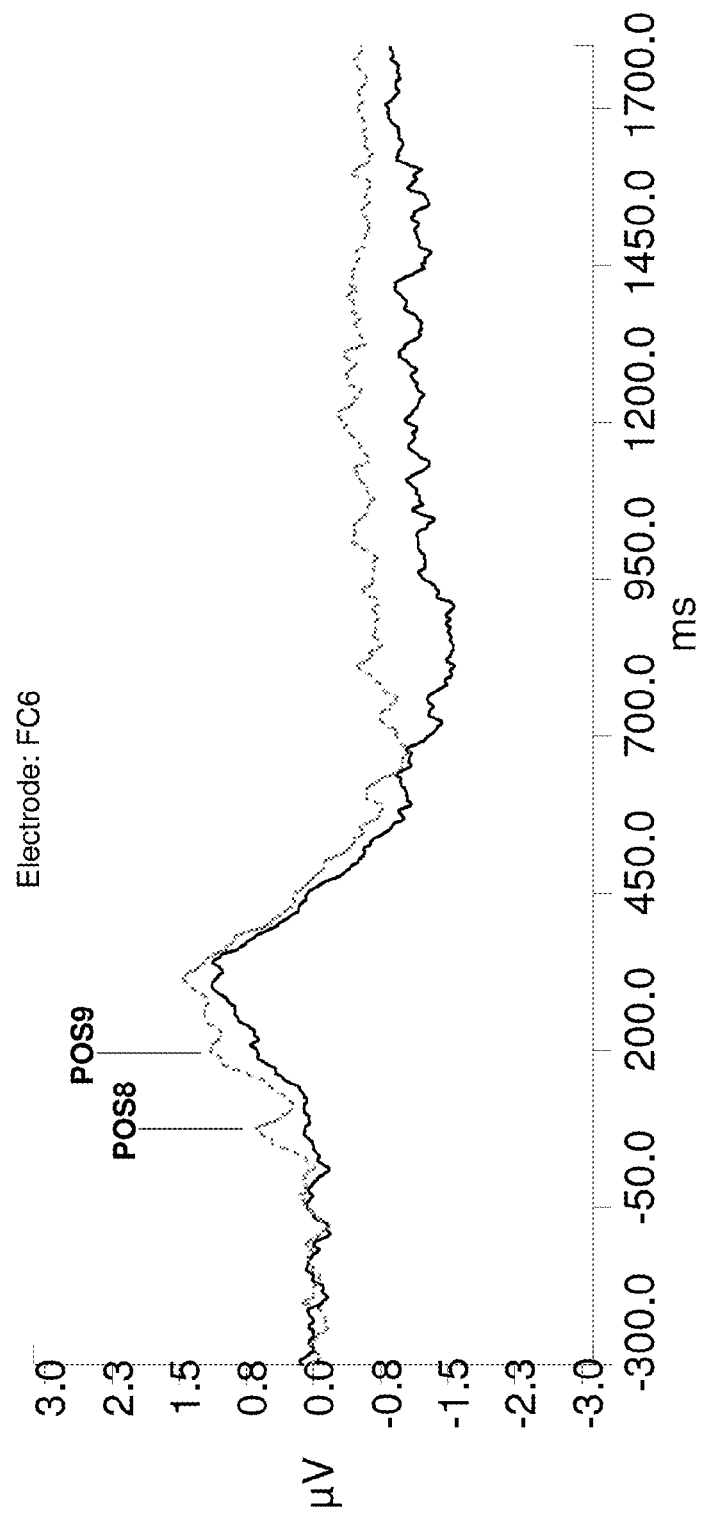
FIG. 23 schematically shows voltage detected in Electrode FC6 vs. time.

8. Pattern POSE: Increased amplitude of a positive peak with peak latency before 150 ms, increased in comparison to that peak in response to other stimuli in the same person. This peak is similar to the auditory P1. This increased amplitude of that peak is present over the right hemisphere in frontal-central locations, and can be measured by electrodes such as FC4, FC6 or similar electrodes. This pattern is illustrated in FIG. 23.

9. Pattern POS9: An increased amplitude of some positive peak (such as auditory P2 or other) that appear between 30-400 ms over the right hemisphere at frontal-central or frontal-temporal locations, and can be measured by FC6 or similar electrodes. The increased amplitude of this peak is in comparison with similar peaks measured in the same electrode in the response to other stimuli in the same person. This pattern is illustrated in FIG. 23.

Figure 24:
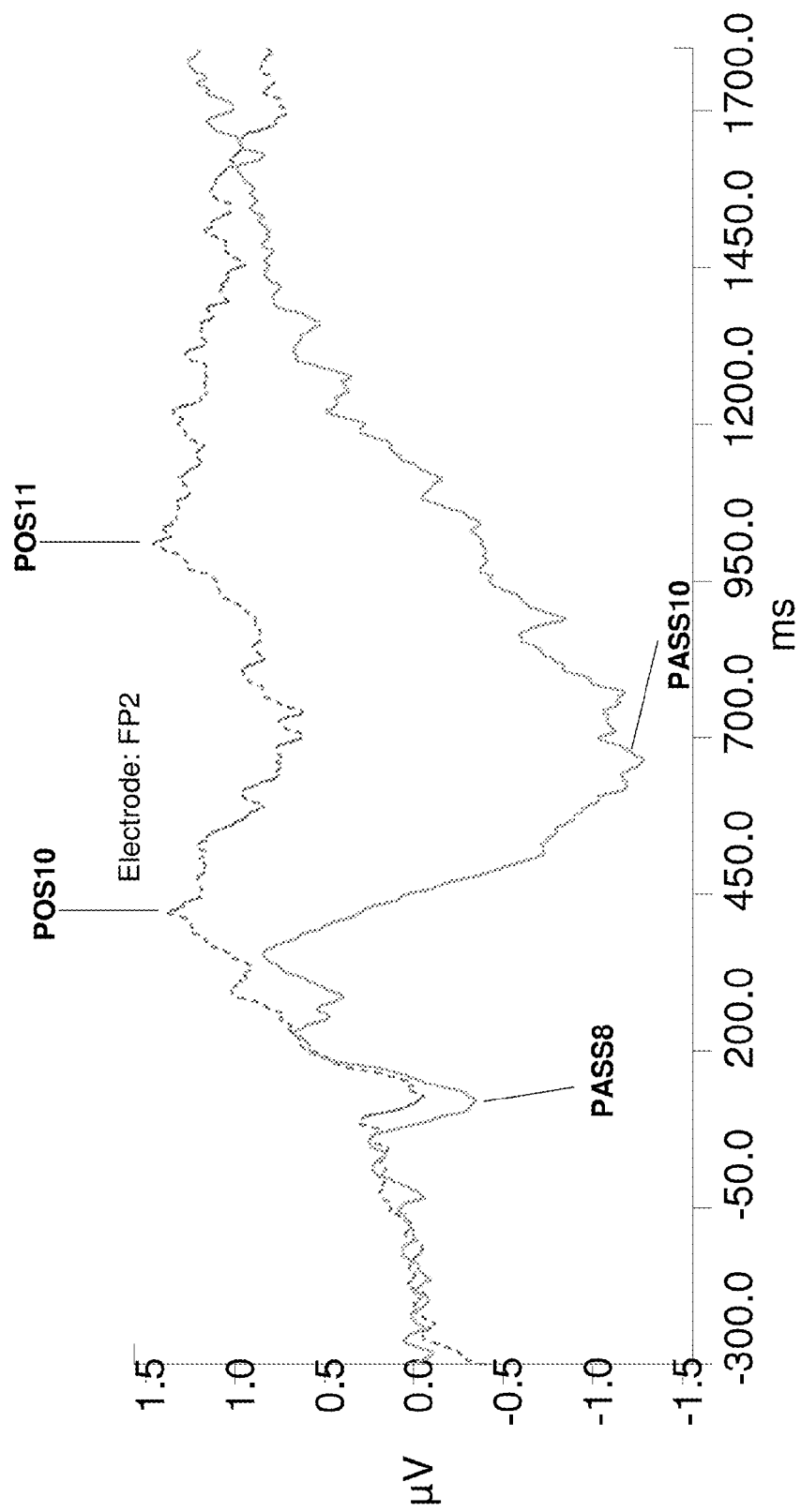
FIG. 24 schematically shows voltage detected in Electrode FP2 vs. time.

10. Pattern POS10: A positive deflection with a maximum peak at latency of 300-600 ms over frontal scalp locations, such as measured by FP1, FP2, FPz or similar electrodes. This pattern is similar to NEG11, but POS10 may have later peak latency and the deflection is longer for POS10. This pattern (POS10) is illustrated in FIG. 24.

11. Pattern POS11: A positive deflection with a maximum peak at latency of 800-1300 ms over frontal scalp locations, such as measured by FP1, FP2, FPz or similar electrodes. This pattern is illustrated in FIG. 24.

12. Additional patterns to the ones described here may be present in response to stimuli with positive personal emotional meaning, and as such may be associated with positive personal emotional meaning.

12. Suggested Methods and Definitions for Pattern Recognition

A 'shift' is present when the complete signal is elevated (positive shift) or lowered (negative shift) in its absolute voltage level over a period of time.

A 'peak' is a local maximum or minimum of the signal, such that its amplitude is greater than a certain measure of the signal.

A. One suggested way to define the peak is such that its absolute amplitude is greater than k*Std+Ave, where—
k=a chosen constant such that k>=1.
Std=standard deviation of the whole signal or part of the signal such as 'baseline' in this electrode in response to this stimulus in this person.
Ave=average of the whole signal or part of the signal in this electrode in response to this stimulus in this person.

B. One suggested common used algorithm for finding positive peaks in the signal can be the following:
  1. Find all local maxima of the signal.
  2. Sort all found maxima by order of amplitude 3. Starting from the greatest maximum remove all maxima that are closer than Twin to that maximum. Twin=a certain chosen time constant such as 10 ms.
  4. Repeat for the rest of the maxima in descending order of amplitude.
  5. The maxima that are left after this procedure are the positive peaks of the signal, each having its peak amplitude and peak latency, in a specific recording electrode.

C. A similar algorithm with the same method may be used for finding negative peaks in the signal, based on finding local minima and following a similar procedure.

D. The following is an additional suggested algorithm to identify the presence of peaks.

This can be used to find patterns with prominent positive or negative peaks appearing over a specific scalp location at specific times.

General Peak Finding Algorithm

1. Find the standard deviation for the part of signal from t=−300 ms to 0 ms ("baseline"; t is the time from stimulus onset, ms—milliseconds. −300 ms is 300 milliseconds before stimulus onset. Min is a minimal amplitude, max is a maximal amplitude. Other time frames may be used as "baseline". It is better to use a time before the stimulus onset.
2. Define "peak sensitivity" as k*std, where std is the standard deviation defined above, and k is a chosen constant, for example k=2; k*std is a required level which defines the max detection vs noise.
3. Define peaks:
  a signal has a max at t=t0 if it falls by at least k*std for t<t0 and for t>t0;
  a signal has a min if it is rises by at least k*std for t<t0 and t>t0.
4. Search for max after min is found; search for min after max is found;

E. The following algorithm may be used to identify whether pattern PASS 1 is present. A similar pattern recognition algorithm may be in use to find other patterns.
1. Record time of occurrence of P2 (The first prominent positive peak that appears after N1, which is the first prominent negative peak of the signal) over frontal locations: electrodes Fz, FCz and etc. Call it tP2; P2 can be found also using one of the algorithms described herein, as the first positive peak identified after the first negative peak of the signal (N1). P1, which occurs before N1, is not present in all cases—for that reason, P2 is the first positive peak identified after N1 in these electrodes, and not just the second positive peak occurring in the signal.

2. Record time of occurrence of the next identified positive peak, after tP2, over the right scalp: electrodes C6, FT8 or other similar electrodes. Call it Pr, and call the time of occurrence tPr. Pr can be identified using one of the algorithms mentioned herein, or some other algorithm.

3. The pattern PASS1 is present if there is at least one electrode in the right scalp for which tP2–tPr time difference is less than 100 ms.

F. The following simplified algorithm may also be used to identify pattern PASS 1:
  1. Find the time of P2 in FCz.
  2. Search if within 100 ms from that time there is an identified peak in electrode C6.
  3. If there is an identified peak in C6 within 100 ms of that time, then pattern
PASS1 is present.

ERP peaks as used here are the prominent peaks of the signal, and may be identified by one of the algorithms given here or by some other algorithms.

G. Other patterns, such as a negative or a positive shift, may be identified in the following way:

A signal is measured over a specific brain area, such as the right frontal, using designated electrodes, such as C6, at a specific time frame after the stimulus onset, such as 250-500 ms.

A specific deflection, such as a "positive shift", is measured by—
1) Measuring the average of the signal for a given period, such as 250-500 ms post stimulus onset;
2) The positive shift is found when the average is greater than k*std, where k is a constant >1, and std is standard deviation of the signal over a period of time such as a 'baseline' before the signal, or some period after, or the whole signal.

H. A pattern of increased amplitude of some peak can be identified when the signal is measured for at least 2 stimuli, at the same person. Then, if a specified peak is found for both stimuli (or for a group of more than 2 stimuli) in the same electrode with a similar latency, and its amplitude is larger significantly for one stimulus than for the other(s), the pattern of increased amplitude of this specific peak is present for this stimulus. This is done by measuring the peak amplitude difference between the 2 stimuli in the same person. One way to identify the presence of this pattern is if this difference is greater than some measure of the signal, such as k*std for a chosen k>0, than the pattern is present. Another way to find if there is a significant difference between the amplitudes of two peaks, for two different stimuli, is by taking the EEG recordings for single repetitions of the stimuli, before averaging the ERP, as described herein, and comparing the amplitudes of the signal in a certain latency—chosen to be the relevant peak latency (defined by the pattern for which increased amplitude is searched) in the ERP after averaging. A statistical test can be conducted for these single measures comparing the amplitudes to two or more stimuli in the same person.

When only one stimulus is recorded, the amplitude of its ERP peaks can be compared to a amplitudes of these peaks that may be given beforehand in a database for similar group of people.

13. Electrode Groups

Some of the more relevant electrodes for identifying patterns related to true, or ultimate passion, or something that the individual truly wants, (with their alternatives) are:
Fpz (or: Fp1, Fp2)
F2 (or: FC2)
FCz (or: Fz)
FT8 (or: T8)
POz (or: Oz, PO3, PO4)

All of the electrodes (out of 10\20 system adapted to 64 channels) relevant to, that can record part of the passion patterns are:
  (1) Right central, frontal central: Fz, F2, F4, FCz, Cz, C2, C4, C6
  (2) Frontal: Fp1, Fp2, Fpz, AF4, AF3
  (3) Right frontal temporal: FT8, T8, TP8, P8
  (4) Left frontal: F3, F1, FC1
  (5) Left frontal temporal: FT7, TP7, P7, P5, PO7
  (6) Parietal Occipital: CB1, O1, Oz, O2, Poz, PO3, PO4

14. Unique Profile of a Person

Each person has a unique profile of response patterns to a given set of stimuli. This profile can be attained by the following method:
Selecting a set of stimuli.
Connecting the person to at least one electrode.
Recording brain response of the subject to the set of stimuli.
Analyzing the brain response pattern to each stimulus.
Using ERP measurement, continuous EEG (qEEG) analysis, or any other analysis of the signal, thus obtaining a set of response patterns to the defined set of stimuli.

This profile can be used to study the person, identify the person, and study his development over time. To certain stimuli (of high importance to the subject), the brain response may stay the same over a period of time. The profile of brain response patterns of a certain person to a certain set of stimuli is typically unique to that person.

This profile can be used for the following purposes:
For identification of the person.
For discrimination between persons.
For psychological or psychiatric assessment of the person.
To define relationships between people.
For research purposes.
To describe the person's responses to a set of objects.
The profile may be obtained in the following way:

A set of stimuli is chosen for the individual person (subject). Stimuli may be: Names and words transmitted verbally to the subject, photos and pictures shown visually to the subject, or any other stimulus transmitted through any of the five modalities, or directly to the brain or nervous system, to the subject.

Optionally, stimuli may include a set of objects that are used by this subject in his everyday life, a set of objects related to important persons in the subject's life, first names, pictures, objects that describe the subject or belong to him or the like.

Optionally, stimuli may include a set of objects related to a study question: objects that the subject's response to them is required from a certain reason, such as but not limited to a set of ideas (religion related words or images), a set of objects or a set of persons' names.

The person is connected to EEG.
EEG is obtained.
The EEG is analyzed, in relation to the stimuli given. For example, the signal is averaged, filtered, cut to periods related to the stimuli. Signal peaks may be characterized by measuring their relative magnitude, width and time delay relative to the stimuli exposure. The energy of the signal is typically summed for example every period of 50 ms.

A set of patterns is obtained for each stimulus used. This set of patterns may be used to identify the person—a distinct set of patterns will be present to the same set of stimuli for another person. This set of patterns can also be used to answer questions about the tested person, connecting the patterns obtained for a stimulus, or a set of stimuli, to a database of patterns and their associated personal meanings, such as the one suggested here.

15. Electrode Localization

A database can be used in order to choose the right localization and combination of EEG electrodes to receive specific information. It is also possible to find the right localization at real time, by measuring the brain response in a set localization, and choosing the combination of electrodes with the optimal brain response at a selected time. The optimal electrode localization on the scalp can be chosen for a certain personal meaning using the following method.

1. EEG electrodes are connected to the tested person.
2. At the time of recording EEG, the tested person is presented with selected stimuli, divided to at least 2 groups of stimuli having different personal meaning to that person, such as—personal-emotional and neutral, familiar and unfamiliar, like and dislike, or some other personal meaning. The personal meaning of those stimuli to the person can be known previously, or determined by some questionnaires such as the ones used here, or by other method of obtaining knowledge. This can also be done through the identification of BAP that are known already as linked to this certain personal meaning previously.
3. Basic ERP analysis is done, such as the one described in this patent application. This is done separately for the 2 groups of stimuli, separately for each tested person.
4. Optimal electrodes are chosen in which the difference between the brain response to the two groups of stimuli is maximal (in latency, peak amplitude, or other measure).
5. A database of electrode combinations is built based on the optimal electrodes for a certain personal meaning.
6. The optimal electrodes chosen can be used for further recordings, in further people with no previous knowledge on their personal meanings.
7. The stimuli selection method is described also herein.

The following is a method to use the database of electrodes localization.

1. Determining the information that is expected to be recorded—or the relevant personal meaning.
2. Choosing from electrode database such as the one included here the electrode combination correspondent to this expected information.
3. Choosing selected stimuli relevant to the information that is expected to be recorded.
4. Attaching the electrodes to the scalp at least at the locations determined by the database, with possible additional locations.
5. Recording EEG from the selected localizations.
6. Administering selected relevant stimuli while recording EEG from the selected electrode combinations.
7. Performing basic EEG analysis to ERP as described here or other analysis, such as gamma band analysis.
8. Identifying BAP in the recorded ERP that are present in a database of BAP and their related personal meanings, such as the one included here.
9. Classifying the test stimuli to groups of personal meanings based on the comparison of the identified BAP to a database of BAP related to specific personal meanings.
10. Giving an output of the extracted personal meaning of a specific stimulus to the user, to a third party or to an application.

16. Electrode Database Example

In this example, the brain response is to facial pictures. The emotional significance of the faces is presented mainly in electrodes in the right parietal region, such as measured by P4, in the conventional 10/20 system.

For partner's facial picture, electrodes in the right frontal region are relevant, such as Fp2, F2, F4, in the conventional 10/20 system.

By analyzing the brain activity from these electrodes, it is possible to find the emotional significance of the face that is shown to the subject.

It is also possible to find whether a specific face is the face of a romantic partner of the person.

The electrode combination found for detecting the subject's partner is described herein.

The electrode combination was selected by selecting the electrodes with the maximal or minimal value for each peak component. Using these electrodes and components, it is possible to detect the subject's partner, out of a list of facial stimuli (different faces shown to the subject while connected to the designated electrodes).

17. Example of a Use to a Specific Pattern from the Database, Comprising of a BAP and an Electrodes Set:

Assuming the following pattern—a positive component (a significant peak with a maximal positive deflection) is present in the latency of 750 ms in response to a facial stimulus, only if the stimulus is familiar, in 15 specific electrodes. Similar patterns are described herein.

1. EEG will be connected and run while the tested person is exposed to the test stimuli.
2. Basic ERP analysis will be done, such as the steps described herein.
3. The brain response of the new tested person will be examined. If a positive component is present in at least 3 of the 15 specific electrodes, and the component is greater than k*std (standard deviation) of the baseline before the stimulus, than the given stimulus is suspected as familiar to that person.

Other possible patterns can be: (1) the response to one group of stimuli (for example familiar), is more focused (the peak appears at the exact same time window in more electrodes), (2) the response involves more electrodes, (3) the response is earlier compared to the response to the other group of stimuli (4) the response is larger (greater peak amplitude) in one group of stimuli compared to another group of stimuli. Other patterns may be present and specified.

18. Detection of Personal-Emotional Words to the Person

1. Potential test words are chosen. Those words can be chosen through an interview with the tested person to collect test words—words that the individual mention, words that are related to his occupation, words that relate to his daily life, words that relate to his hobbies, words that relate to his dreams, or any other common words in the language, or words out of his curriculum vitae, or words suggested by a third party or from a database.

a. The words are divided to lists—words related to fear, words related to wishes, words from curriculum vitae, etc.

2. Audio files are prepared out of the selected words, or audio files are selected from a given database of recorded audio words.
3. The patient is connected to EEG electrodes.
4. Recording EEG while the subject hears or sees the words.
5. Analyzing ERP or other analysis out of the recorded EEG.
6. Identifying BAP and electrode combinations.
7. Using a given database of BAP related to personal meanings such as the one proposed here—with known or given information—what does the individual wish for, what does the individual fear from, what does the individual want, what is personal—emotional to the individual, the data from a specific measurement is compared to the given database.

8. The personal meanings of the test words is determined upon comparison to the given database of BAP and their associated personal meanings.

The given database of BAP can be built using people tested in the same paradigm, with known information regarding the personal meaning of each word in their words list from beforehand.

APPENDIX

The following questions can be used as well to help determine a personal meaning of a stimulus to a person, to be connected to new BAP. The answers can be given on any scale, such as the one suggested here of 1-5, 5 being the maximal response:

---

Is it strange to you?
Is it related to traumatic memories?
Is it emotional to you?
Rate each word using the questions below, on a scale of 1-5.
(1 = very much, 5 = not at all)
1. How important is that word for you?
2. How much do you think about it daily?
3. How significant is this thing for you?
4. How much is it something that you want or desire?
5. How bad is it for you?
6. How disturbing is it for you?
7. How much is it present in your life?
8. How much do you want more of it?
9. How much do you think it is an important thing in general?
10. How good do you think that thing is?
11. How much has this thing affected your life?
12. How bad do you think that thing is?
13. How much has this thing hurt you?
14. Would you prefer not to have this thing in your life?
15. How much is it part of your life?
16. Has this thing ever appeared in your dreams?
17. How often does this thing come to your mind?
18. How important is this concept to you?
19. How important is it in your life?
If the word is related to an event
20. How much do you think of that event?
21. How much was this event meaningful to you?
22. How much did this event effect your life?
23. How significant was this event for you?

---

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for identifying a personal meaning of a stimulus to an examinee, wherein said personal meaning is conscious or unconscious to said examinee, the method comprising:

exposing said examinee to at least one stimulus;
providing a measuring system capable of measuring Electro-Encephalo-Graphy ("EEG"), including at least one recording electrode;
measuring EEG signals using said measuring system;
providing a processor to process EEG;
processing the measured EEG using said processor to process EEG, extracting Event Related Potentials ("ERP") in response to a stimulus that is presented to said examinee;
determining whether at least one predefined pattern can be identified in said ERP in response to said stimulus, wherein the predefined pattern is characterized by at least one of:
a) prominent positive deflection over the right hemisphere with peak latency at a time between 200-500 milliseconds from stimulus onset;
b) prominent negative deflection with peak amplitude over the right hemisphere in frontal or temporal locations with peak latency between 500-900 milliseconds;
c) enhanced amplitude of at least one common appearing positive or negative peak of an ERP response to said stimulus, in comparison with the ERP response to other stimuli in said examinee, or in comparison with a selected averaged ERP response to stimuli, including peaks P1-N1-P2 or other peaks, as commonly defined in the relevant literature, wherein P1 is the first occurring positive deflection in the ERP response and N1 is the first occurring prominent negative deflection in the ERP response and P2 is the second occurring prominent positive deflection in the ERP response, occurring after N1;
d) enhanced amplitude of a negative peak with a latency between 200-500 milliseconds, in comparison with the amplitude of a similar peak in the ERP response to other stimuli in said examinee, or in comparison with a similar peak amplitude in a selected averaged ERP response to stimuli; or
e) another certain voltage deflection over a certain scalp area that can be shown to be related to a certain personal emotional meaning; and inferring the personal meaning of said stimulus to said examinee based on the identification of said at least one predefined pattern in said ERP, wherein said personal meaning is selected from a group consisting of: positive personal emotional meaning, negative personal emotional meaning, and person passion.

2. The method of claim 1, wherein said personal meaning is a positive personal emotional meaning, and is inferred by the identification of a predefined pattern that comprises prominent positive deflection over the right hemisphere with peak latency at a time between 200-500 milliseconds from stimulus onset.

3. The method of claim 2, wherein said predefined pattern has a maximal peak within 100 milliseconds after the peak of an auditory frontal P2, wherein said auditory frontal P2 is measured for said examinee in response to an auditory stimulus over frontal locations by at least one electrode selected from the group consisting of Fz, FCz and similar electrodes over frontal scalp locations as stated by the common 10/20 system adapted to 64 channels, or a similar system of electrodes, and said auditory frontal P2 is measured as the second prominent positive deflection in such electrode, and said predefined pattern is identified in said ERP of said examinee to said stimulus, thus inferring a positive personal emotional meaning of said stimulus to said examinee.

4. The method of claim 3, wherein said predefined pattern is prominent over the right hemisphere and is measured by at least one electrode selected from the group consisting of F8, T8, FT8, and similar electrodes over right frontal or temporal scalp locations, as stated by the common 10/20 system adapted to 64 channels, or a similar system of electrodes, and said predefined pattern is identified in said ERP of said examinee to said stimulus, thus inferring a positive personal emotional meaning of said stimulus to said examinee.

5. The method of claim 2, wherein said predefined pattern features peak amplitude over the right frontal or temporal scalp, and is measured by at least one electrode selected from the group consisting of F8, T8, FT8 and other electrodes on right frontal or temporal scalp locations, as stated by the common 10/20 system adapted to 64 channels, or a similar system of electrodes, and said predefined pattern is identified in said ERP of said examinee to said stimulus, thus inferring a positive personal emotional meaning of said stimulus to said examinee.

6. The method of claim 1, wherein the personal meaning is a positive personal emotional meaning, and said predefined pattern comprises a prominent negative deflection with peak amplitude over the right hemisphere in frontal or temporal locations with peak latency between 500-900 milliseconds from stimulus onset, and said predefined pattern is identified in said ERP of said examinee to said stimulus, thus inferring a positive personal emotional meaning of said stimulus to said examinee.

7. The method of claim 6, wherein said predefined pattern is prominent over the right hemisphere in frontal or temporal locations, and is measured by at least one electrode selected from the group consisting of F8, T8, FT8, C6, and other electrodes over frontal or temporal locations, as stated by the common 10/20 system adapted to 64 channels, or a similar system of electrodes, and said predefined pattern is identified in said ERP of said examinee to said stimulus, thus inferring a positive personal emotional meaning of said stimulus to said examinee.

8. The method of claim 7, wherein the measured peak latency for said predefined pattern is 600-800 milliseconds from stimulus onset, and said predefined pattern is identified in said ERP of said examinee to said stimulus, thus inferring a positive personal emotional meaning of said stimulus to said examinee.

9. The method of claim 1, wherein said personal meaning is personal passion in relation with said stimulus, and said predefined pattern comprises enhanced amplitude of a common appearing positive or negative peak of an ERP response to stimuli including peaks P1-N1-P2, as commonly defined in the relevant literature, wherein P1 is the first occurring positive deflection in the ERP response and N1 is the first occurring prominent negative deflection in the ERP response and P2 is the second occurring prominent positive deflection in the ERP response occurring after N1.

10. The method of claim 9, wherein said predefined pattern comprises enhanced amplitude of a peak in the ERP response to stimuli, with a peak latency between 50-350 milliseconds from stimulus onset, over a location selected from the group consisting of frontal, temporal, central and occipital locations, and said predefined pattern is identified in the ERP of said examinee to said stimulus, thus inferring a meaning of personal passion in relation with said stimulus for said examinee.

11. The method of claim 10, wherein said predefined pattern is measured as prominent over a location selected from the group consisting of frontal, temporal, central and occipital locations, and is measured by at least one electrode selected from the group consisting of FPz, FP2, Fz, FCz, FC3, FC4, Cz, CP2, FC4, TP7; CP5, FT7, FT8, Oz, POz, O2, and other electrodes over similar scalp locations, as stated by the common 10/20 system adapted to 64 electrodes, or a similar system of electrodes, and said predefined pattern is identified in said ERP of said examinee to said stimulus, thus inferring a personal emotional meaning of personal passion in relation with said stimulus for said examinee.

12. The method of claim 11, wherein when a measuring system capable of measuring EEG is provided, and the EEG responses to several stimuli are recorded in said examinee using said measuring system, and a processor capable of processing EEG is provided, and the EEG is processed to extract ERP, as commonly defined in the relevant literature, using said processor separately for each stimulus, and the peak amplitude of at least one ERP peak between 50-350 milliseconds from stimulus onset is enhanced for at least one stimulus when compared to similar peaks, with similar latencies measured in the same electrode for other stimuli in said examinee, then said at least one stimulus, to which said at least one ERP peak is enhanced compared to the other stimuli, is identified as being related to personal passion more than the other stimuli presented to said examinee.

13. The method of claim 1, wherein said personal meaning is a negative personal emotional meaning, and said predefined pattern comprises enhanced amplitude of a negative peak with a latency between 200-500 milliseconds, in comparison with the amplitude of a similar peak in the ERP response to other stimuli in said examinee, or in comparison with a similar peak amplitude in some averaged ERP response to stimuli, and said predefined pattern is identified in said ERP of said examinee to said stimulus, thus inferring a negative personal emotional meaning of said stimulus to said examinee.

14. The method of claim 13, wherein said predefined pattern of enhanced amplitude of said negative peak is identified over parietal or occipital scalp locations, and a negative personal emotional meaning of said stimulus to said examinee is inferred.

15. The method of claim 14, wherein said predefined pattern is identified as prominent over parietal or occipital scalp locations and is measured by at least one electrode selected from the group of P3, PO7, PO3, P1, O1, Oz, O2 and similar electrodes over parietal or occipital scalp locations, as stated by the common 10/20 system of electrodes adapted to 64 channels, or a similar system of electrodes, and said predefined pattern is identified in said ERP of said examinee to said stimulus, thus inferring a negative personal emotional meaning of said stimulus to said examinee.

16. The method of claim 15, wherein when the response to several stimuli is recorded in said examinee, and the peak amplitude of a negative peak between 200-500 milliseconds over parietal or occipital scalp locations is enhanced for at least one stimulus when compared to similar peaks with similar latencies measured in the same electrode for other stimuli in said examinee, then said at least one stimulus to which said negative peak is enhanced compared to the other stimuli is identified as having negative personal emotional meaning more than the other stimuli presented to said examinee.

17. The method of claim 1, wherein a cluster of more than one predefined pattern is used to infer the personal meaning of the stimulus to said examinee based on the personal meaning that is more related to said cluster of more than one predefined pattern.

18. The method of claim 1, wherein if said predefined pattern is identified for more than one stimulus, then the stimulus, to which the peak amplitude of said predefined pattern is the greatest among said more than one stimulus, is inferred as more related to the personal meaning associated with that said predefined pattern than the other stimuli presented to said examinee.

19. The method of claim 1, wherein when a measuring system capable of measuring EEG is provided, and the EEG responses to several stimuli are recorded in said examinee using said measuring system, and a processor capable of processing EEG is provided, and the EEG is processed to extract ERP, as commonly defined in the relevant literature, using said processor separately for each stimulus, and the peak amplitude of at least one ERP peak between 50-350 milliseconds from stimulus onset is enhanced for at least one stimulus when compared to similar peaks with similar latencies measured in the same electrode for other stimuli in said examinee, then said at least one stimulus to which said at least one ERP peak is enhanced compared to the other stimuli, is identified as being related to personal passion more than the other stimuli presented to said examinee.

\* \* \* \* \*